US012797346B2

(12) United States Patent
Fraser et al.

(10) Patent No.: US 12,797,346 B2
(45) **Date of Patent: *Nov. 17, 2026**

(54) INHALABLE EPINEPHRINE FORMULATION

(71) Applicant: De Motu Cordis Pty Ltd, Windsor (AU)

(72) Inventors: John Fraser, Windsor (AU); Sean Dalziel, Red Hill (AU); Teresa Iley, Hertfordshire (GB); Jonathan Brazier, Hertfordshire (GB); Patrick Joseph Lynch, Windsor (AU); John Fredatovich, Windsor (AU); Benjamin Barnaby Trout, Windsor (AU)

(73) Assignee: De Motu Cordis Pty Ltd, Windsor (AU)

( * ) Notice: Subject to any disclaimer, the term of this patent is extended or adjusted under 35 U.S.C. 154(b) by 229 days.

This patent is subject to a terminal disclaimer.

(21) Appl. No.: 18/672,318

(22) Filed: May 23, 2024

(65) Prior Publication Data

US 2024/0342117 A1 Oct. 17, 2024

Related U.S. Application Data

(63) Continuation of application No. 17/886,124, filed on Aug. 11, 2022, now Pat. No. 12,029,709.

(51) Int. Cl.

| | |
|---|---|
| ***A61K 31/137*** | (2006.01) |
| ***A61K 9/00*** | (2006.01) |
| ***A61K 47/26*** | (2006.01) |

(52) U.S. Cl.
CPC .......... *A61K 31/137* (2013.01); *A61K 9/0075* (2013.01); *A61K 47/26* (2013.01)

(58) Field of Classification Search
CPC ..... A61K 31/137; A61K 9/0075; A61K 47/26
See application file for complete search history.

(56) References Cited

U.S. PATENT DOCUMENTS

| | | | | |
|---|---|---|---|---|
| 8,920,781 | B2 | 12/2014 | Staniforth | |
| 9,980,904 | B2 | 5/2018 | Dalvi et al. | |
| 12,029,709 | B2 * | 7/2024 | Fraser .................... | A61K 47/26 |
| 2004/0076588 | A1 | 4/2004 | Batycky et al. | |
| 2016/0220489 | A1 | 8/2016 | Fleming et al. | |
| 2016/0263027 | A1 | 9/2016 | Pasquali et al. | |
| 2017/0119699 | A1 | 5/2017 | Batycky et al. | |
| 2018/0056022 | A1 | 3/2018 | Liu et al. | |
| 2021/0283050 | A1 | 9/2021 | Temtsin-Krayz et al. | |
| 2022/0087938 | A1 | 3/2022 | Savmarker et al. | |

FOREIGN PATENT DOCUMENTS

| | | | |
|---|---|---|---|
| WO | 01/60341 | A1 | 8/2001 |
| WO | 2009088553 | A1 | 7/2009 |
| WO | 2021/186437 | A1 | 9/2021 |
| WO | 2022261453 | A1 | 12/2022 |

OTHER PUBLICATIONS

International Search Report for PCT/AU2023/050756, mailed Oct. 5, 2023.
Written Opinion of the International Searching Authority for PCT/AU2023/050756, mailed Oct. 5, 2023.
Rahimpour et al., "Lactose Engineering for Better Performance in Dry Powder Inhalers", Advanced Pharmaceutical Bulletin (2012), vol. 2(2), pp. 183-187.
Hovione FarmaCiencia SA, Process Development, Spray drying technology for better API crystals, Retrived online Mar. 8, 2023.

* cited by examiner

*Primary Examiner* — Mina Haghighatian
(74) *Attorney, Agent, or Firm* — Hoffmann & Baron, LLP

(57) ABSTRACT

The present disclosure relates to an inhalable formulation, suitable for use in a dry powder inhaler, for the delivery of epinephrine, or a pharmaceutically acceptable salt or derivative thereof. The inhalable formulation further comprises a solid carrier and results in a stable formulation with useful physical properties for delivery to the lungs of a subject in need of epinephrine.

11 Claims, 7 Drawing Sheets

A. B.

A. B.

INHALABLE EPINEPHRINE FORMULATION

This application is a Continuation Application which claims benefit from U.S. Ser. No. 17/886,124 filed Aug. 11, 2022, which is incorporated herein by reference in its entirety.

TECHNICAL FIELD

This disclosure relates to an inhalable formulation comprising epinephrine, or a pharmaceutically acceptable derivative and/or salt thereof, and a dry powder inhaler containing the inhalable formulation.

BACKGROUND

Anaphylaxis is a severe, potentially life-threatening allergic reaction. It can be caused by a number of triggers including: certain foods, such as nuts, shellfish or eggs; insect venom, such as bee or wasp stings; certain medications, such as antibiotics or aspirin; general anaesthetics and latex. As a first response to the trigger, the immune system releases a flood of chemicals that can cause the body to go into shock. Common signs and symptoms of anaphylaxis include a rapid, weak pulse; swelling of the lips, tongue or throat; shortness of breath and difficulty breathing; skin rashes and itching; and stomach pain, nausea and vomiting. If the condition is not treated immediately, it can be fatal.

The primary treatment of anaphylaxis is the administration of epinephrine. Epinephrine, also known as adrenaline, is a hormone and neurotransmitter that stimulates the sympathetic nervous system. There are several treatment methods for anaphylaxis using epinephrine which are currently known. Arguably the most well-known product is the EpiPen, an auto-injector for the self-administration of epinephrine. The subject is required to jab (inject) him- or herself with the needle (preferably in the thigh), resulting in the release of a set dose of epinephrine into the muscle tissue.

While the technology certainly has benefits, one major downside of this product is the harshness of the treatment method. Many patients and caregivers are reluctant to inject themselves with a needle, consequently wasting essential time in the context of an emergent life-threatening reaction. Further, the hesitancy to administer epinephrine via intramuscular injection gives rise to less than optimal decision making—such as 'wait and see', or treat first with an oral anti-histamine approaches. The use of an auto-injector device also carries the risk of accidental needle injury.

Dry powder inhalers (DPIs) in combination with inhalable dry powders are used in the treatment of diseases such as respiratory diseases, cardiovascular diseases, diabetes, obesity, and cancer, or symptoms associated with these and other diseases, for example, nausea, vomiting, pain, and inflammation by delivering a consistent dose of a pharmacological agent to the patients' airways through inhalation.

However, DPIs present challenges in terms of suitable formulations that have the appropriate particle sizes containing the active ingredient and which maintain this throughout a reasonable storage time. It is essential to achieve the necessary balance between the components of the formulation so that the active ingredient can be delivered to the deep lungs to provide for a suitably rapid response time.

SUMMARY

In a first aspect, the disclosure resides in an inhalable formulation comprising:

(i) epinephrine, and/or a pharmaceutically acceptable derivative and/or salt thereof; and (ii) a solid carrier.

In embodiments, the epinephrine, and/or a pharmaceutically acceptable derivative and/or salt thereof, is present at between about 0.01 to about 15.0 mg per unit dose of the formulation.

In embodiments, the epinephrine salt or epinephrine derivative salt is selected from the group consisting of the bitartrate, hydrochloride, maleate, malate, malonate, fumarate, and borate salts, and mixtures thereof.

In embodiments, the epinephrine derivative is selected from the group consisting of norepinephrine, dopamine, 3-methoxytyramine, synephrine, p-octopamine and salts and mixtures thereof.

In embodiments, the solid carrier is selected from the group consisting of sugars and sugar alcohols, including saccharides and polysaccharides, such as lactose, mannose, sucrose, mannitol, trehalose, citrates, amino acids such as glycine, L-leucine, isoleucine, trileucine, tartrates, methionine, vitamin A, zinc citrate, trisodium citrate, zinc chloride, polyvinylpyrrolidone, phospholipids including diphosphotidylcholine and the like.

In an embodiment, the solid carrier is selected from the group consisting of lactose monohydrate, anhydrous lactose, sucrose, mannitol and trehalose.

When the solid carrier comprises lactose it may be in the α-form, the β-form, or a mixture thereof, and may be crystalline.

When the solid carrier comprises lactose it may be in the monohydrate or anhydrous form.

In embodiments, the solid carrier is a powdered solid carrier.

In embodiments, the inhalable formulation of the first aspect is a dry powder inhalable formulation.

In embodiments of the first aspect, the inhalable formulation or dry powder inhalable formulation consists of or consists essentially of epinephrine, or a pharmaceutically acceptable derivative or salt thereof, and a solid carrier.

In a preferred embodiment, the inhalable formulation does not comprise any excipients other than the solid carrier.

In a second aspect, the disclosure resides in a container comprising the inhalable formulation of the first aspect.

The container may be a capsule, a cartridge, a blister, a blister strip, or other suitable container which, when filled with the formulation of the first aspect, can be loaded into a dry powder inhaler.

In a third aspect, the disclosure resides in a dry powder inhaler comprising the inhalable formulation of the first aspect.

In embodiments, the dry powder inhaler of the second aspect may be as described in any embodiment disclosed in WO2020/257845 and/or WO2020/257843, which are hereby incorporated by reference in their entirety.

In a fourth aspect, the disclosure resides in a process of forming the inhalable formulation of the first aspect, including the steps of:

(a) micronizing epinephrine, or pharmaceutically acceptable derivative or salt thereof, and (b) combining the micronized epinephrine, or pharmaceutically acceptable derivative or salt thereof, with a solid carrier.

In a fifth aspect, the disclosure resides in the inhalable formulation of the first aspect, when produced by the process of the fourth aspect.

In a sixth aspect, the disclosure resides in a method of delivering epinephrine, and/or a pharmaceutically acceptable derivative and/or salt thereof, to a subject in need thereof, including the step of:

administering the inhalable formulation of the first aspect to the subject, to thereby deliver the epinephrine, and/or a pharmaceutically acceptable derivative and/or salt thereof, to the subject.

In embodiments, the method of delivering epinephrine, and/or a pharmaceutically acceptable derivative and/or salt thereof, to the subject includes the steps of:

providing the inhalable formulation of the first aspect to the subject; and allowing the subject to inhale the inhalable formulation, to thereby deliver the epinephrine, and/or a pharmaceutically acceptable derivative and/or salt thereof, to the subject.

In embodiments, the step of providing the inhalable formulation of the first aspect may include providing the dry powder inhaler of the third aspect to the subject.

In embodiments, the step of providing the inhalable formulation of the first aspect may include at least partially filling a container with the inhalable formulation.

In embodiments, the method of delivering epinephrine, and/or a pharmaceutically acceptable derivative and/or salt thereof, to a subject further includes the step of loading the container into the dry powder inhaler of the third aspect.

In embodiments, the method of delivering epinephrine, and/or a pharmaceutically acceptable derivative and/or salt thereof, to a subject is a method of delivering epinephrine, and/or a pharmaceutically acceptable derivative and/or salt thereof, to the lungs of a subject.

In a seventh aspect, the disclosure resides in a method of preventing or treating a disease, disorder or condition responsive to epinephrine, and/or a pharmaceutically acceptable derivative and/or salt thereof, in a subject in need thereof, including the step of:

administering the inhalable formulation of the first aspect to the subject;

to thereby prevent or treat the disease, disorder or condition in the subject.

In embodiments, the disease, disorder or condition responsive to epinephrine, and/or a pharmaceutically acceptable derivative and/or salt thereof, is selected from the group consisting of anaphylaxis, cardiac arrest, glaucoma, asthma, bronchospasm, croup, and respiratory distress.

In embodiments, the method of the seventh aspect includes the steps of:

providing the inhalable formulation of the first aspect to the subject; and allowing the subject to inhale the inhalable formulation, to thereby treat the disease or condition in the subject.

In embodiments, the step of providing the inhalable formulation of the first aspect may include providing the dry powder inhaler of the third aspect to the subject.

In embodiments, the method of the seventh aspect further includes the steps of: (i) monitoring the patient; and (ii) optionally administering further amounts of the inhalable formulation of the first aspect.

Each aspect or embodiment as defined herein may be combined with any other aspect(s) or embodiment(s) unless clearly indicated otherwise.

DESCRIPTION OF EMBODIMENTS

Figure 1:
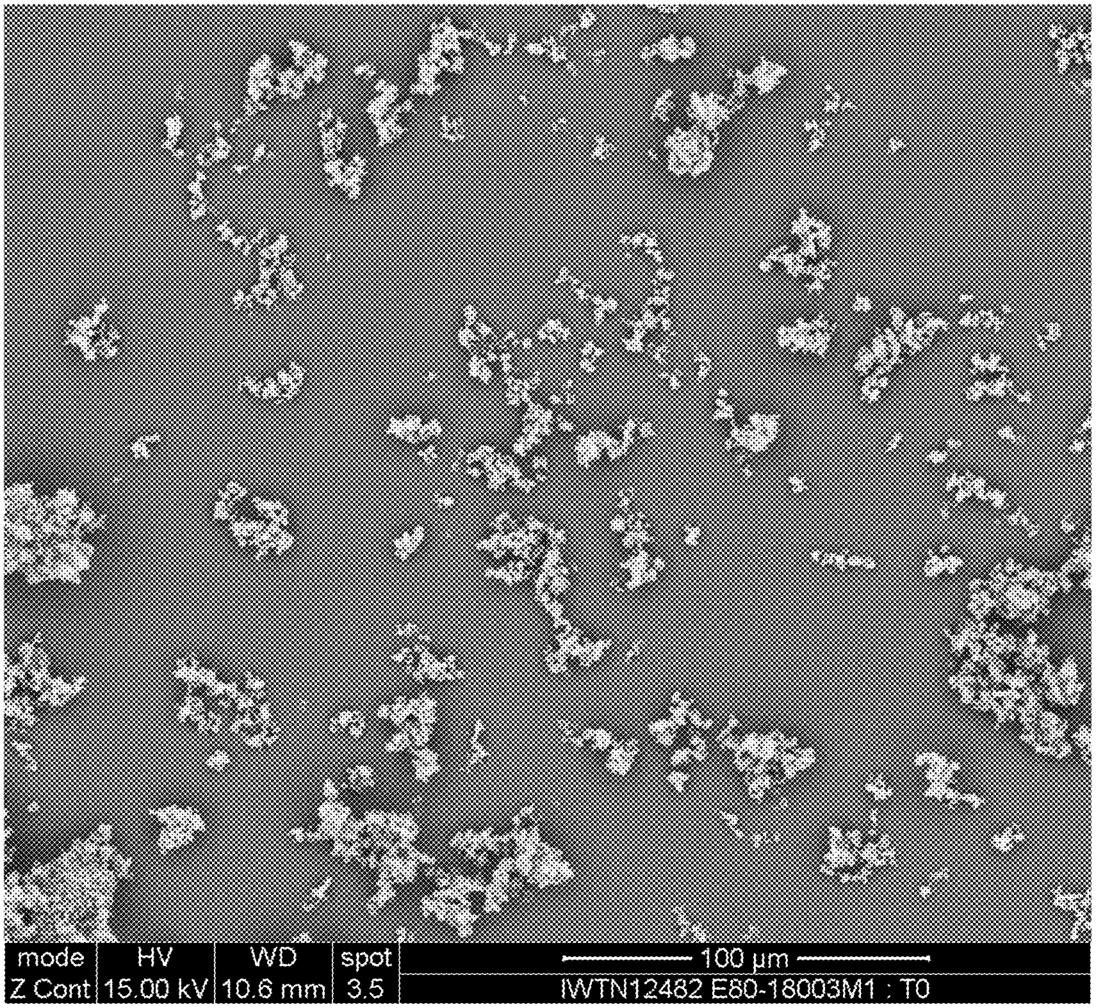
FIG. 1: shows a SEM (scanning electron microscope) image of the particle size distribution of micronized epinephrine bitartrate at an initial time point.

It will be appreciated by the person of skill in the art that epinephrine and adrenaline are two accepted terms for the same active pharmaceutical ingredient (API) and references herein to epinephrine can be considered references to adrenaline. That is, the terms may be used interchangeably herein. Further the term epinephrine may refer to a single pure enantiomer of epinephrine, such as R-epinephrine, or racemic epinephrine (containing 1:1 proportions of the R- and S-enantiomers), or mixtures of any ratio of the enantiomers of epinephrine.

The present disclosure describes how an inhalable epinephrine formulation can be uniquely tailored for delivery via a dry powder inhaler (DPI) to a subject's lungs to treat or prevent a condition, disorder or disease responsive to epinephrine. It has been surprisingly found that a simple formulation of epinephrine, and/or a pharmaceutically acceptable derivative and/or salt thereof, with a solid carrier provides for a stable composition, with useful aerodynamic particle size distribution characteristics, without the requirement for further force control, lubricating, flow or other agents or excipients. Further the use of fines of the carrier (e.g., lactose fines) to assist in the deagglomeration of epinephrine bitartrate from alpha lactose monohydrate was found not to be necessary to achieve an aerodynamic particle size distribution useful for inhalation delivery of epinephrine.

In a first aspect, the disclosure resides in an inhalable formulation comprising:

(i) epinephrine, and/or a pharmaceutically acceptable derivative and/or salt thereof; and (ii) a solid carrier.

In embodiments, the epinephrine, and/or a pharmaceutically acceptable derivative and/or salt thereof, is a crystalline epinephrine, and/or a pharmaceutically acceptable derivative and/or salt thereof.

In embodiments, the epinephrine, and/or a pharmaceutically acceptable derivative and/or salt thereof is a crystalline epinephrine, or a pharmaceutically acceptable salt thereof.

In embodiments, the epinephrine, and/or a pharmaceutically acceptable derivative and/or salt thereof, is present within the inhalable formulation at between about 0.01 to about 15.0 mg per unit dose of the formulation. For example, a unit dose of the formulation of the first aspect may comprise epinephrine, and/or a pharmaceutically acceptable derivative and/or salt thereof, at between about 0.01 to about 14.0 mg, between about 0.01 to about 13.0 mg, between about 0.01 to about 12.0 mg, between about 0.01 to about 11.0 mg, between about 0.01 to about 10.0 mg, between about 0.01 to about 9.0 mg, between about 0.01 to about 8.0 mg, between about 0.01 to about 7.0 mg, between about 0.01 to about 6.0 mg, between about 0.01 to about 5.0 mg, between about 0.01 to about 4.5 mg, between about 0.01 to about 4.0 mg, between about 0.01 to about 3.5 mg, between about 0.01 to about 3.0 mg, or at between about 0.025 to about 15.0 mg, at between about 0.025 to about 14.0 mg, at between about 0.025 to about 13.0 mg, at between about 0.025 to about 12.0 mg, at between about 0.025 to about 11.0 mg, at between about 0.025 to about 10.0 mg, at between about 0.025 to about 9.0 mg, at between about 0.025 to about 8.0 mg, at between about 0.025 to about 7.0 mg, at between about 0.025 to about 6.0 mg, at between about 0.025 to about 5.0 mg, between about 0.025 to about 4.5 mg, between about 0.025 to about 4.0 mg, between about 0.025 to about 3.5 mg, between about 0.025 to about 3.0 mg, or at between about 0.05 to about 15.0 mg, at between about 0.05 to about 14.0 mg, at between about 0.05 to about 13.0 mg, at between about 0.05 to about 12.0 mg, at between about 0.05 to about 11.0 mg, at between about 0.05 to about 10.0 mg, at between about 0.05 to about 9.0 mg, at between about 0.05 to about 8.0 mg, at between about 0.05 to about 7.0 mg, at between about 0.05 to about 6.0 mg, at between about 0.05 to about 5.0 mg, between about 0.05 to about 4.5 mg, between about 0.05 to about 4.0 mg, between about 0.05 to about 3.5 mg, between about 0.05 to about 3.0 mg, or at between about 0.1 to about 15.0 mg, at between about 0.1 to about 14.0 mg, at between about 0.1 to about 13.0 mg, at between about 0.1 to about 12.0 mg, at between about 0.1 to about 11.0 mg, at between about 0.1 to about 10.0 mg, at between about 0.1 to about 9.0 mg, at between about 0.1 to about 8.0 mg, at between about 0.1 to about 7.0 mg, at between about 0.1 to about 6.0 mg, at between about 0.1 to about 5.0 mg, between about 0.1 to about 4.5 mg, between about 0.1 to about 4.0 mg, between about 0.1 to about 3.5 mg, between about 0.1 to about 3.0 mg, or at between about 0.25 to about 15.0 mg, at between about 0.25 to about 14.0 mg, at between about 0.25 to about 13.0 mg, at between about 0.25 to about 12.0 mg, at between about 0.25 to about 11.0 mg, at between about 0.25 to about 10.0 mg, at between about 0.25 to about 9.0 mg, at between about 0.25 to about 8.0 mg, at between about 0.25 to about 7.0 mg, at between about 0.25 to about 6.0 mg, at between about 0.25 to about 5.0 mg, between about 0.25 to about 4.5 mg, between about 0.25 to about 4.0 mg, between about 0.25 to about 3.5 mg, between about 0.25 to about 3.0 mg, or at between about 0.3 to about 15.0 mg, at between about 0.3 to about 14.0 mg, at between about 0.3 to about 13.0 mg, at between about 0.3 to about 12.0 mg, at between about 0.3 to about 11.0 mg, at between about 0.3 to about 10.0 mg, at between about 0.3 to about 9.0 mg, at between about 0.3 to about 8.0 mg, at between about 0.3 to about 7.0 mg, at between about 0.3 to about 6.0 mg, at between about 0.3 to about 5.0 mg, between about 0.3 to about 4.5 mg, between about 0.3 to about 4.0 mg, between about 0.3 to about 3.5 mg, between about 0.3 to about 3.0 mg, or at between about 0.5 to about 15.0 mg, at between about 0.5 to about 14.0 mg, at between about 0.5 to about 13.0 mg, at between about 0.5 to about 12.0 mg, at between about 0.5 to about 11.0 mg, at between about 0.5 to about 10.0 mg, at between about 0.5 to about 9.0 mg, at between about 0.5 to about 8.0 mg, at between about 0.5 to about 7.0 mg, at between about 0.5 to about 6.0 mg, at between about 0.5 to about 5.0 mg, between about 0.5 to about 4.5 mg, between about 0.5 to about 4.0 mg, between about 0.5 to about 3.5 mg, between about 0.5 to about 3.0 mg.

It will be appreciated by a person of skill in the art that the unit dose of the epinephrine, and/or a pharmaceutically acceptable derivative and/or salt thereof, will be determined by the end application. For example, in the treatment of asthma, using the inhalable formulation of the first aspect at a dose of approximately 0.05 to 0.1 mg epinephrine may be sufficient when appropriately delivered. For use in treating anaphylaxis the required dose may be between about 0.1 to 1.0 mg for some pediatric use or between about 1.0 to 2.0 mg for some adult treatment dosage ranges. These factors along with typical therapeutic dosing considerations such as the subject's age, weight and general health would be considered by a skilled formulator or physician and the dose selected accordingly.

It will be appreciated by a person of skill in the art that a much higher dose of the inhalable formulation of the first aspect may be used when treating anaphylactic shock in a patient. The dose may be between about 1.0 to 15.0 mg, or between about 3.0 to 15.0 mg, or between about 5.0 to 15.0 mg. It may be even necessary to give one or more further doses of the inhalable formulation of the first aspect.

In embodiments, the epinephrine salt or epinephrine derivative salt is selected from the group consisting of the bitartrate, hydrochloride, maleate, malate, malonate, fumarate, and borate salts, and mixtures thereof.

While the free base form of epinephrine may be used it has been found that a salt form can provide significant further advantages in stability of the formulation.

In embodiments, the epinephrine derivative, or salt thereof, is selected from the group consisting of norepinephrine, dopamine, 3-methoxytyramine, synephrine, p-octopamine and salts and mixtures thereof.

In preferred embodiments, the epinephrine, and/or a pharmaceutically acceptable derivative and/or salt thereof, is epinephrine or a pharmaceutically acceptable salt thereof. However, it will be appreciated that certain derivatives of epinephrine, or salts thereof, may be present as impurities or even degradation products which will not negatively impact upon the efficacy of the inhalable formulation to any significant degree. For example, norepinephrine may be present in the formulation at less than about 2.5% w/w, or less than about 1.5% w/w, or less than about 1.0% w/w, or less than about 0.5% w/w.

In embodiments, the solid carrier is present within the inhalable formulation of the first aspect at between 25% w/w to 99% w/w of the entire formulation. For example, the formulation of the first aspect may comprise a solid carrier at between 30% w/w to 99% w/w, or at between 35% w/w to 99% w/w, or at between 40% w/w to 99% w/w, or at between 45% w/w to 99% w/w, or at between 50% w/w to 99% w/w, or at between 55% w/w to 99% w/w, at between 60% w/w to 99% w/w, or at between 65% w/w to 99% w/w, or at between 70% w/w to 99% w/w, or at between 75% w/w to 99% w/w, or at between 80% w/w to 99% w/w, or at between 85% w/w to 99% w/w, or at between 30% w/w to 98% w/w, or at between 35% w/w to 98% w/w, or at between 40% w/w to 98% w/w, or at between 45% w/w to 98% w/w, or at between 50% w/w to 98% w/w, or at between 55% w/w to 98% w/w, or at between 60% w/w to 98% w/w, or at between 65% w/w to 98% w/w, or at between 70% w/w to 98% w/w, or at between 75% w/w to 98% w/w, or at between 80% w/w to 98% w/w, or at between 85% w/w to 98% w/w, or at between 30% w/w to 97% w/w, or at between 35% w/w to 97% w/w, or at between 40% w/w to 97% w/w, or at between 45% w/w to 97% w/w, or at between 50% w/w to 97% w/w, or at between 55% w/w to 97% w/w, or at between 60% w/w to 97% w/w, or at between 65% w/w to 97% w/w, or at between 70% w/w to 97% w/w, or at between 75% w/w to 97% w/w, or at between 80% w/w to 97% w/w, or at between 85% w/w to 97% w/w, or at between 30% w/w to 96% w/w, or at between 35% w/w to 96% w/w, or at between 40% w/w to 96% w/w, or at between 45% w/w to 96% w/w, or at between 50% w/w to 96% w/w, or at between 55% w/w to 96% w/w, or at between 60% w/w to 96% w/w, or at between 65% w/w to 96% w/w, or at between 70% w/w to 96% w/w, or at between 75% w/w to 96% w/w, or at between 80% w/w to 96% w/w, or at between 85% w/w to 96% w/w, or at between 30% w/w to 95% w/w, or at between 35% w/w to 95% w/w, or at between 40% w/w to 95% w/w, or at between 45% w/w to 95% w/w, or at between 50% w/w to 95% w/w, or at between 55% w/w to 95% w/w, or at between 60% w/w to 95% w/w, or at between 65% w/w to 95% w/w, or at between 70% w/w to 95% w/w, or at between 75% w/w to 95% w/w, or at between 80% w/w to 95% w/w, or at between 85% w/w to 95% w/w.

In embodiments, the solid carrier is present within the inhalable formulation of the first aspect at between 85% w/w to 95% w/w, or at between 85% w/w to 94% w/w, or at between 85% w/w to 93% w/w, or at between 85% w/w to 92% w/w, or at between 86% w/w to 95% w/w, or at between 86% w/w to 94% w/w, or at between 86% w/w to 93% w/w, or at between 86% w/w to 92% w/w, or at between 87% w/w to 95% w/w, or at between 87% w/w to 94% w/w, or at between 87% w/w to 93% w/w, or at between 87% w/w to 92% w/w, or at between 88% w/w to 95% w/w, or at between 88% w/w to 94% w/w, or at between 88% w/w to 93% w/w, or at between 88% w/w to 92% w/w.

In another preferred embodiment, when the inhalable formulation is directed to pediatric use, the solid carrier may be present within the inhalable formulation of the first aspect at between 90% w/w to 99% w/w, or at between 90% w/w to 98% w/w, or at between 90% w/w to 97% w/w, or at between 90% w/w to 96% w/w, or at between 91% w/w to 99% w/w, or at between 91% w/w to 98% w/w, or at between 91% w/w to 97% w/w, or at between 91% w/w to 96% w/w, or at between 92% w/w to 99% w/w, or at between 92% w/w to 98% w/w, or at between 92% w/w to 97% w/w, or at between 92% w/w to 96% w/w, or at between 93% w/w to 99% w/w, or at between 93% w/w to 98% w/w, or at between 93% w/w to 97% w/w, or at between 93% w/w to 96% w/w, or at between 94% w/w to 99% w/w, or at between 94% w/w to 98% w/w, or at between 94% w/w to 97% w/w, or at between 94% w/w to 96% w/w.

In a preferred embodiment, when the solid carrier of the inhalable formulation of any embodiment of the first aspect is a lactose monohydrate and/or an anhydrous lactose solid carrier, optionally a crystalline lactose monohydrate and/or a crystalline anhydrous lactose, the lactose monohydrate and/or the anhydrous lactose solid carrier is present within the inhalable formulation of the first aspect at between 25% w/w to 99% w/w, or at between 30% w/w to 99% w/w, or at between 35% w/w to 99% w/w, or at between 40% w/w to 99% w/w, or at between 45% w/w to 99% w/w, or at between 50% w/w to 99% w/w, or at between 55% w/w to 99% w/w, or at between 60% w/w to 99% w/w, or at between 65% w/w to 99% w/w, or at between 70% w/w to 99% w/w, or at between 75% w/w to 99% w/w, or at between 80% w/w to 99% w/w, or at between 85% w/w to 99% w/w, or at between 30% w/w to 98% w/w, or at between 35% w/w to 98% w/w, or at between 40% w/w to 98% w/w, or at between 45% w/w to 98% w/w, or at between 50% w/w to 98% w/w, or at between 55% w/w to 98% w/w, or at between 60% w/w to 98% w/w, or at between 65% w/w to 98% w/w, or at between 70% w/w to 98% w/w, or at between 75% w/w to 98% w/w, or at between 80% w/w to 98% w/w, or at between 85% w/w to 98% w/w, or at between 30% w/w to 97% w/w, or at between 35% w/w to 97% w/w, or at between 40% w/w to 97% w/w, or at between 45% w/w to 97% w/w, or at between 50% w/w to 97% w/w, or at between 55% w/w to 97% w/w, or at between 60% w/w to 97% w/w, or at between 65% w/w to 97% w/w, or at between 70% w/w to 97% w/w, or at between 75% w/w to 97% w/w, or at between 80% w/w to 97% w/w, or at between 85% w/w to 97% w/w, or at between 30% w/w to 96% w/w, or at between 35% w/w to 96% w/w, or at between 40% w/w to 96% w/w, or at between 45% w/w to 96% w/w, or at between 50% w/w to 96% w/w, or at between 55% w/w to 96% w/w, or at between 60% w/w to 96% w/w, or at between 65% w/w to 96% w/w, or at between 70% w/w to 96% w/w, or at between 75% w/w to 96% w/w, or at between 80% w/w to 96% w/w, or at between 85% w/w to 96% w/w, or at between 30% w/w to 95% w/w, or at between 35% w/w to 95% w/w, or at between 40% w/w to 95% w/w, or at between 45% w/w to 95% w/w, or at between 50% w/w to 95% w/w, or at between 55% w/w to 95% w/w, or at between 60% w/w to 95% w/w, or at between 65% w/w to 95% w/w, or at between 70% w/w to 95% w/w, or at between 75% w/w to 95% w/w, or at between 80% w/w to 95% w/w, or at between 85% w/w to 95% w/w. In another preferred embodiment, the lactose monohydrate and/or the anhydrous lactose solid carrier is present within the inhalable formulation of the first aspect at between 85% w/w to 95% w/w, or at between 85% w/w to 94% w/w, or at between 85% w/w to 93% w/w, or at between 85% w/w to 92% w/w, or at between 86% w/w to 95% w/w, or at between 86% w/w to 94% w/w, or at between 86% w/w to 93% w/w, or at between 86% w/w to 92% w/w, or at between 87% w/w to 95% w/w, or at between 87% w/w to 94% w/w, or at between 87% w/w to 93% w/w, or at between 87% w/w to 92% w/w, or at between 88% w/w to 95% w/w, or at between 88% w/w to 94% w/w, or at between 88% w/w to 93% w/w, or at between 88% w/w to 92% w/w.

In another preferred embodiment, when the inhalable formulation is directed to pediatric use, the lactose monohydrate and/or the anhydrous lactose solid carrier may be present within the inhalable formulation of the first aspect at between 90% w/w to 99% w/w, or at between 90% w/w to 98% w/w, or at between 90% w/w to 97% w/w, or at between 90% w/w to 96% w/w, or at between 91% w/w to 99% w/w, or at between 91% w/w to 98% w/w, or at between 91% w/w to 97% w/w, or at between 91% w/w to 96% w/w, or at between 92% w/w to 99% w/w, or at between 92% w/w to 98% w/w, or at between 92% w/w to 97% w/w, or at between 92% w/w to 96% w/w, or at between 93% w/w to 99% w/w, or at between 93% w/w to 98% w/w, or at between 93% w/w to 97% w/w, or at between 93% w/w to 96% w/w, or at between 94% w/w to 99% w/w, or at between 94% w/w to 98% w/w, or at between 94% w/w to 97% w/w, or at between 94% w/w to 96% w/w.

The aerodynamic particle size distribution is a key parameter to consider to ensure delivery of the inhalable formulation to the deep lungs. Particles with diameters greater than 5 μm generally deposit in the mouth, throat or upper airways whereas articles with a diameter of less than 0.5 μm do not settle out of the airflow to deposit in the lungs, and are subsequently exhaled immediately. It has been advantageously found that the inhalable formulations of the present disclosure provide for a useful particle size profile for delivery of the epinephrine active to the lung.

In embodiments, the median particle size distribution by volume (Dv50) of epinephrine, and/or the pharmaceutically acceptable derivative and/or salt thereof, is between about 0.5 μm to about 5 μm. In an embodiment, the Dv50 value of epinephrine, and/or the pharmaceutically acceptable derivative and/or salt thereof, is between 1 μm to about 4 μm, or between 1 μm to about 3 μm, or between 2 μm to about 3 μm.

In another embodiment, the maximum particle diameter below which 90% of epinephrine, and/or the pharmaceutically acceptable derivative and/or salt thereof, exists (Dv90) is between about 2 μm to about 5 μm. In an embodiment, the Dv90 value of epinephrine, and/or the pharmaceutically acceptable derivative and/or salt thereof, is between 3 μm to about 4 μm.

A range of solid carriers suitable to inhalation formulations are known in the art. In embodiments, the solid carrier may be selected from the group consisting of sugars, sugar alcohols, citrates, amino acids and peptides, vitamins and other suitable solid carriers.

When the solid carrier is a sugar or sugar alcohol, it may be selected from the group consisting of lactose, mannose, sucrose, mannitol and trehalose.

When the solid carrier is a citrate it may be selected from the group consisting of zinc citrate and trisodium citrate.

When the solid carrier is an amino acid or peptide it may be selected from the group consisting of glycine, L-leucine, isoleucine, methionine and trileucine.

When the solid carrier is a vitamin it may be vitamin A.

Other suitable carriers may include zinc chloride, polyvinylpyrrolidone, and diphosphotidylcholine and the like.

In an embodiment, the solid carrier is selected from the group consisting of alpha-lactose monohydrate, beta-lactose, anhydrous lactose, mannitol, sucrose, and trehalose.

When the solid carrier comprises lactose it may be in the α-form, the β-form, or a mixture thereof, and may be crystalline in either form.

It will be appreciated by a person of skill in the art that the α-lactose form can exist as both a monohydrate and an anhydrous form. Further, the β-form generally exists as an anhydrous form only, not a hydrate. When the solid carrier comprises lactose it may be in any of these forms both singularly and in any combination. For example, the solid carrier may comprise α-lactose in both monohydrate and anhydrous forms with or without the anhydrous β-form being present. In combination with all of these embodiments of α- and/or β-lactose, the lactose may be in crystalline or amorphous forms. It may be preferred that any α- and/or β-lactose forms are crystalline.

In embodiments, the solid carrier is a powdered solid carrier.

The solid carrier, optionally lactose solid carrier, may have a particle size distribution as follows: D10 between 20 to 45 μm, optionally between 25 to 35 μm; D50 between 50 to 70 μm, optionally between 55 to 65 μm; and D90 between 75 to 105 μm, optionally between 85 to 100 μm. In embodiments the solid carrier is the commercially available Respitose SV003 provided by DFE Pharma, although similar grades of lactose solid carrier would also be suitable.

In preferred embodiments of the first aspect, the solid carrier comprises or consists of or consists essentially of a crystalline solid carrier.

In embodiments, the majority of the solid carrier is in crystalline form. Crystalline carriers are preferable for the present inhalable formulation as they reduce processing complexity and are thermodynamically more stable than amorphous carriers. The use of a crystalline sold carrier means there is no need for a pharmaceutical spray dryer, the solid carrier is therefore not constrained to spray drying amenable materials only, the stability thermodynamics may be improved in the crystalline state, and the crystalline epinephrine may be less hygroscopic than amorphous epinephrine forms.

In embodiments, the inhalable formulation of the first aspect is a dry powder inhalable formulation. That is, all of the components of the formulation for delivery to a subject are in a substantially dry powder form.

In embodiments of the first aspect, the solid carrier consists or consists essentially of lactose monohydrate and/or anhydrous lactose, optionally crystalline lactose monohydrate and/or crystalline anhydrous lactose.

In certain examples, the dry powder inhalable formulation comprises, consists or consists essentially of:

(i) a pharmaceutically acceptable salt of epinephrine, optionally the bitartrate salt of epinephrine; and (ii) a lactose-based solid carrier, optionally a lactose monohydrate and/or an anhydrous lactose solid carrier, optionally a crystalline lactose monohydrate and/or a crystalline anhydrous lactose.

The epinephrine and lactose carrier may be as described in any previous embodiment or combination thereof.

In embodiments of the first aspect, the inhalable formulation or dry powder inhalable formulation consists of or consists essentially of epinephrine, and/or a pharmaceutically acceptable derivative and/or salt thereof; and a solid carrier.

Typically, a number of other excipients and carriers have to be added to dry powder formulations to achieve the desired properties, such as desired stability of the formulation, the right aerodynamic particle size distribution and the necessary anti-agglomeration properties of the particles. This may be particularly so for epinephrine which can be challenging to formulate while maintaining stability, preventing reactions with one or more of the formulation components and avoiding significant agglomeration and clumping of the formulation. It has surprisingly been found that it is not necessary to add any further excipients other than the chosen solid carrier to the epinephrine, or pharmaceutically acceptable salt thereof, to form the inhalable formulation of the present disclosure and to achieve the described benefits. Further, it was not necessary to add a fines fraction of the carrier excipient to assist the de-agglomeration of API from carrier particles. The inhalable formulation described herein therefore does not require a delivery device which has been particularly designed with a focus on achieving deagglomeration of clumps of dry powder. Such devices can be complex, require expensive manufacturing and may often not be successful in the deagglomeration process thereby resulting in poor delivery of the active agent. The simplicity of the inhalable formulation described herein is a significant advantage of the present invention while maintaining the described advantages.

In embodiments of the first aspect, the inhalable formulation does not comprise any agent which could be considered to be or which plays an active role as an excipient, a second carrier material, a flow control agent, a lubricant, a force control agent, a pH buffering agent, or other additive which assists in delivery of the active epinephrine form, other than the recited solid carrier.

In any embodiment of the present disclosure, the inhalable formulation of the first aspect does not comprise a pH buffering agent, such as sodium dihydrogen phosphate.

While a buffering agent may be required for formulations to be delivered intranasally they are not required for the present formulation which is designed for delivery to the lungs via a DPI.

Therefore, when the inhalable formulation of the first aspect comprises epinephrine bitartrate and lactose monohydrate it does not comprise sodium dihydrogen phosphate.

Therefore, in examples, the inhalable formulation of the first aspect comprises: (i) epinephrine, and/or a pharmaceutically acceptable derivative and/or salt thereof, optionally epinephrine bitartrate; and (ii) a single excipient which is a solid carrier. Optionally, the single excipient which is a solid carrier is a lactose carrier such as lactose monohydrate and/or an anhydrous lactose. The lactose carrier may comprise any ratio of α- and β-lactose forms and may be crystalline, amorphous or a mixture thereof. Crystalline lactose forms may, in certain examples, be preferred.

In embodiments, the inhalable formulation comprises: (i) epinephrine, and/or a pharmaceutically acceptable derivative and/or salt thereof, optionally epinephrine bitartrate; and (ii) lactose monohydrate and/or an anhydrous lactose.

In any embodiment of the first aspect, the epinephrine, and/or a pharmaceutically acceptable derivative and/or salt thereof is crystalline micronized epinephrine bitartrate.

In embodiments, the crystalline micronized epinephrine bitartrate has not been formed by a spray drying process.

The combination of epinephrine with lactose has been found to be especially advantageous as an inhalable formulation. Epinephrine alone was found to have a strong tendency to agglomerate. This is a major risk factor for a dry powder inhaler formulation since agglomeration of particles greatly increases the particle size and significantly reduces the percentage of the API that is successfully delivered to the deep lung. Particularly, it was found that crystalline micronized epinephrine bitartrate alone would form agglomerates and it was expected that various glidants and/or anti-agglomerating agents would be required in addition to a solid carrier or that complex processing approaches, such as spray drying, would be necessary. As described in the Examples, it has surprisingly been found the inhalable formulation of the present invention shows minimal signs of agglomeration when epinephrine is used purely in combination with a lactose carrier. Therefore, it has been found that the inhalable formulation of the present invention is extremely stable in aerodynamic particle size distribution over an extended period of time and provides for a desirable sustained FPF for delivery to a subject.

As discussed above, this is a significant and unexpected advantage in that further processing steps or particular storage processes do not have to be implemented to the extent they would for an inhalable formulation which does tend to naturally agglomerate. Additionally, the inhalable formulation of the first aspect does not require delivery only by specified dry powder inhalers which are designed with component parts or chambers which have a purpose of deagglomerating clumped dry powder formulation. This could not have been expected with an epinephrine formulation when crystalline micronized epinephrine, such as epinephrine bitartrate, is demonstrated to naturally form significant agglomerates. The challenge of avoiding or reducing epinephrine agglomeration could further not have been expected to be solved by a single carrier, and particularly by a lactose carrier for reasons further discussed below.

Without wishing to be bound by theory, this unexpected effect may be due to the lactose having an unexpectedly strong stabilizing effect on the epinephrine particle size distribution during long term storage where, otherwise, the epinephrine, particularly epinephrine bitartrate, would readily self-agglomerate and so require further processing prior to loading or specialized equipment for delivery to a subject.

Other challenges to be aware of when creating pharmaceutical formulations are undesired side reactions, such as the Maillard reaction. The Maillard reaction is a chemical reaction between an amine (such as epinephrine) and a reducing sugar (such as lactose). This reaction gives a distinct browning color development in the powder as the degradation reaction proceeds and may be problematic with epinephrine formulations. To prevent this reaction, further additives such as antioxidants are usually added. In the food industry, these additives are usually sulfite compounds, such as sulfur dioxide or salts containing metabisulfite, which are known triggers for asthma, even inhaled at low levels. It is therefore particularly surprising that a lactose solid carrier could be used alone with epinephrine bitartrate to solve the above-mentioned problems of agglomeration while not resulting in stability or storage difficulties based on an expected reaction between the two components. The combination of an epinephrine salt with a reducing sugar, as a solid carrier, as the only two components of a formulation would not be a solution which would present itself naturally to a skilled formulator based upon the inherent problems it would be expected to bring about. The present inhalable formulation does not require or comprise an antioxidant.

It may therefore be especially advantageous and surprising that the inhalable formulation of the present invention, particularly when lactose is the solid carrier, does not show any tendency to undergo side reactions. As demonstrated in the Examples, the inhalable formulation has a high chemical stability even after 6 months of storage and shows no signs of Maillard browning degradation despite the lack of an antioxidant excipient.

In embodiments, the inhalable formulation consists of or consists essentially of:

(i) epinephrine, and/or a pharmaceutically acceptable derivative and/or salt thereof; and (ii) lactose monohydrate and/or an anhydrous lactose.

In embodiments, the inhalable formulation consists of or consists essentially of: (i) epinephrine bitartrate; and (ii) α-lactose monohydrate and/or anhydrous α-lactose, optionally the epinephrine bitartrate is crystalline epinephrine bitartrate including micronized crystalline epinephrine bitartrate, optionally the α-lactose monohydrate and/or anhydrous α-lactose are crystalline.

In embodiments, the inhalable formulation does not contain lactose fines in addition to the solid carrier. Lactose fines are milled and micronized lactose particles. They are usually added to a dry powder inhaler formulation as a separate grade of lactose (processed via milling, micronization, sieving, classification, or other means of producing a powder with substantially smaller particle sizes than standard grades of lactose). Lactose fines are added to various pharmaceutical product DPI formulations to help the disagglomeration and dispersion of fine API particles from the solid carrier particles within the aerosol and, therefore, improve the delivery of the API to the deep lungs. While a small amount of lactose fines in the inhalable formulation of the present disclosure may be useful or moderately beneficial, it is an advantage that it is not necessary to add lactose fines to epinephrine DPI formulations of the first aspect to achieve a pharmaceutically useful aerodynamic particle size distribution, flowability, and to minimize aggregation. Surprisingly, the inhalable formulation of the present invention shows the desired delivery properties to the deep lung when regular particle size lactose (Respitose®) is used.

In embodiments when the inhalable formulation comprises lactose fines they are present at less than 20% w/w, or less than 15% w/w, or less than 10% w/w, or less than 5% w/w, or less than 3% w/w, or less than 1.5% w/w of the entire formulation.

In a preferred embodiment, the inhalable formulation does not comprise magnesium stearate. Magnesium stearate is a common lubricant excipient added to dry powder formulations to improve aerosol performance and resistance to moisture. It may be especially advantageous that the inhalable formulation of the present invention does not need addition of magnesium stearate to show the desired properties. It is generally expected in the field that to achieve a suitable aerodynamic particle size distribution of such epinephrine and solid carrier formulations, a lubricant is required to reduce adherence of the powder formulation to the container and any device surfaces, and to assist in consistent processing of the encapsulation step during manufacture of capsules. It was found that the inhalable formulations of the first aspect do not require this additional functionality of magnesium stearate or any other lubricant in order to satisfy the required parameters and, indeed, may benefit by their absence.

In a second aspect, the disclosure resides in a container comprising the inhalable formulation of the first aspect.

The container may be a capsule, a cartridge, a blister, a blister strip, or other suitable container which, when filled with the formulation of the first aspect, can be loaded into a dry powder inhaler.

Such containers are well-known in the art and will vary depending on the manner in which the formulation is to be released from the container during an inhalation operation using the appropriate delivery device. In one embodiment, the container may be a capsule suitable to be pierced by one or more actuators within the delivery device. The container may be as described in WO2020/257845 and/or WO2020/257843, although it will be appreciated the present invention is not so limited.

In a third aspect, the disclosure resides in a dry powder inhaler comprising the inhalable formulation of the first aspect and/or the container of the second aspect.

In embodiments, the dry powder inhaler of the third aspect may be as described in any embodiment disclosed in WO2020/257845 and/or WO2020/257843, which are hereby incorporated by reference in their entirety.

In embodiments, the inhalable formulation of the first aspect is provided in capsules, as described for the second aspect, that are designed for use in the dry powder inhaler of the third aspect.

In a fourth aspect, the disclosure resides in a process of forming the inhalable formulation of the first aspect, including the steps of:

(a) micronizing the epinephrine, and/or pharmaceutically acceptable derivative and/or salt thereof, and
(b) combining the micronized epinephrine, and/or pharmaceutically acceptable derivative and/or salt thereof, with the solid carrier.

In embodiments, the step of micronizing the epinephrine may be carried out using cryogenic micronization or ambient temperature micronization approaches. It is one advantage of the present disclosure that cryogenic micronization, while useful, is not a requirement to achieve a useful formulation.

In embodiments, the micronized epinephrine, and/or pharmaceutically acceptable derivative and/or salt thereof, and the solid carrier are passed through a sieve before being combined.

In embodiments, the combining step is a step of dry blending the solid carrier with the micronized epinephrine, and/or pharmaceutically acceptable derivative and/or salt thereof.

In embodiments, the median particle size distribution (Dv50) of the epinephrine, or the pharmaceutically acceptable derivative or salt thereof, is between about 0.5 μm to about 5 μm or between 1 μm to about 4 μm, or between 1 μm to about 3 μm, or between 1.5 μm to about 3 μm after micronization.

In embodiments, the median particle size distribution (Dv50) of the epinephrine, or the pharmaceutically acceptable derivative or salt thereof, is about 2.0 μm. It has been advantageously found that this particle size distribution can be maintained in storage stably for at least a period of one month.

In embodiments, the inhalable formulation of the first aspect can be blended by either low shear or high shear blending techniques. It is an advantage of the formulation of the first aspect that the requirements are very low in terms of the need for tight processing controls of any critical process parameters in the intensity or time of blending. This affords a robust process that can be more readily scaled-up compared to a process that may have more process parameter criticality or sensitivity over how the API and solid carrier are blended. For example, the process of the fourth aspect does not require a spray drying step.

In embodiments, the process of the fourth aspect further comprises a step of packing the inhalable formulation in suitable containers of the second aspect for use in the dry powder inhaler of the third aspect.

In a fifth aspect, the disclosure resides in the inhalable formulation of the first aspect, when produced by the process of the fourth aspect.

In a sixth aspect, the disclosure resides in a method of delivering epinephrine, and/or a pharmaceutically acceptable derivative and/or salt thereof, to a subject in need thereof, including the step of:

administering the inhalable formulation of the first aspect to the subject, to thereby deliver the epinephrine, and/or a pharmaceutically acceptable derivative and/or salt thereof, to the subject.

In embodiments, the method of delivering epinephrine, and/or a pharmaceutically acceptable derivative and/or salt thereof, to the subject includes the steps of:

providing the inhalable formulation of the first aspect to the subject; and allowing the subject to inhale the inhalable formulation, to thereby deliver the epinephrine, and/or a pharmaceutically acceptable derivative and/or salt thereof, to the subject.

In embodiments, the step of providing the inhalable formulation of the first aspect may include providing the dry powder inhaler of the third aspect to the subject.

In embodiments, the step of providing the inhalable formulation of the first aspect may include at least partially filling a container with the inhalable formulation.

In embodiments, the method of delivering epinephrine, and/or a pharmaceutically acceptable derivative and/or salt thereof, to a subject further includes the step of loading the container into the dry powder inhaler of the third aspect.

In embodiments, the method of delivering epinephrine to a subject is a method of delivering epinephrine to the respiratory tract and, particularly, to the lungs of a subject.

It may be especially advantageous to treat a subject with the inhalable formulation of the first aspect. The unique properties of the inhalable formulation, such as the anti-agglomeration properties and the aerodynamic particle size distribution, allow the epinephrine, and/or the pharmaceutically acceptable derivative and/or salt thereof, to travel to the deep lung through inhalation without depositing in the upper airways and the throat.

In embodiments, the method of delivering epinephrine to a subject is a method of self-administering the inhalable formulation to the respiratory tract by using the dry powder inhaler of the third aspect.

In a seventh aspect, the disclosure resides in a method of treating or preventing a disease, disorder or condition responsive to epinephrine, and/or a pharmaceutically acceptable derivative and/or salt thereof, in a subject in need thereof, including the step of:

administering the inhalable formulation of the first aspect to the subject;

to thereby treat or prevent the disease, disorder or condition in the subject.

The unique properties of the inhalable formulation allow the epinephrine, and/or the pharmaceutically acceptable derivative and/or salt thereof, to reach the deep lung without delay and, therefore, the method of the seventh aspect is a quick and convenient way of treating a disease, disorder or condition responsive to epinephrine.

In embodiments, the disease, disorder or condition responsive to epinephrine, and/or a pharmaceutically acceptable derivative and/or salt thereof, is selected from the group consisting of anaphylaxis, cardiac arrest, glaucoma, asthma, bronchospasm, croup, and respiratory distress.

In embodiments, the method of the seventh aspect includes the steps of:

providing the inhalable formulation of the first aspect to the subject; and allowing the subject to inhale the inhalable formulation, to thereby treat or prevent the disease, disorder or condition in the subject.

In embodiments, the step of providing the inhalable formulation of the first aspect may include providing the dry powder inhaler of the third aspect to the subject.

In embodiments, the step of allowing the subject to inhale the inhalable formulation includes a substantial proportion of the inhalable formulation reaching the lungs of the subject as a result of the inhalation.

In embodiments, the method of the seventh aspect further includes the steps of: (i) monitoring the patient; and (ii) optionally administering further amounts of the inhalable formulation of the first aspect.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXPERIMENTAL

Example 1: Composition of Inhalable Epinephrine Formulations With Lactose Monohydrate as Carrier Table 1 shows six epinephrine formulations that were each blended using a Turbula mixer (low shear type mixer). Each formulation contains crystalline micronized epinephrine bitartrate and alpha-lactose monohydrate (Respitose SV003).

TABLE 1

Epinephrine Blend Compositions.

| Blend Code | Epinephrine (% w/w) | Material | Mass (g) |
|---|---|---|---|
| 1A | 1.2% | Epinephrine Bitartrate | 2.183 |
| | | alpha-lactose monohydrate (Respitose SV003) | 97.817 |
| 1B | 1.2% | Epinephrine Bitartrate | 2.185 |
| | | alpha-lactose monohydrate (Respitose SV003) | 97.815 |
| 1C | 4% | Epinephrine Bitartrate | 7.277 |
| | | alpha-lactose monohydrate (Respitose SV003) | 92.723 |
| 1D | 6% | Epinephrine Bitartrate | 10.927 |
| | | alpha-lactose monohydrate (Respitose SV003) | 89.073 |
| 1E | 12% | Epinephrine Bitartrate | 21.831 |
| | | alpha-lactose monohydrate (Respitose SV003) | 78.169 |
| 1F | 12% | Epinephrine Bitartrate | 21.853 |
| | | alpha-lactose monohydrate (Respitose SV003) | 78.147 |

Blends 1A, 1B, 1C, 1D, and 1E were filled into size 3 HPMC capsules containing 25 mg of blend each. The 1.2%, 4%, 6% and 12% blends correspond to capsule strengths of 0.3 mg, 1.0 mg, 1.5 mg and 3.0 mg epinephrine, respectively.

Example 2: Composition of Inhalable Epinephrine Formulations With Mannitol as Carrier Tables 2 and 3 show theoretical and actual inhalable formulations of crystalline epinephrine bitartrate with mannitol as a carrier.

TABLE 2

Theoretical inhalable epinephrine compositions with mannitol as carrier.

| Epinephrine (% w/w) | Material | Theoretical Amount (g) |
|---|---|---|
| 1.2% | Epinephrine Bitartrate | 2.183 |
| | Mannitol | 97.817 |
| 4% | Epinephrine Bitartrate | 7.277 |
| | Mannitol | 92.723 |
| 12% | Epinephrine Bitartrate | 21.831 |
| | Mannitol | 78.169 |

TABLE 3

Actual inhalable epinephrine composition with mannitol as carrier.

| Blend Code | Epinephrine (% w/w) | Material | Actual Amount (g) |
|---|---|---|---|
| 2A | 12% | Epinephrine Bitartrate | 2.85* |
| | | Mannitol | 10.15 |

*The target drug substance mass of 2.838 g was adjusted to 2.85 g to account for epinephrine potency of the specific lot of epinephrine bitartrate drug substance used in the experiment.

Upon achieving acceptable blending, the formulations were further processed by filling in to glass vials for stability testing. No issues were encountered in performing the powder handling transfers from bulk blend to filled vials.

Example 3: Compositions of Inhalable Epinephrine Formulations With Trehalose as Carrier Table 4 and 5 show examples of the theoretical and actual inhalable epinephrine compositions with trehalose as carrier.

TABLE 4

Theoretical inhalable epinephrine compositions with trehalose as carrier.

| Epinephrine (% w/w) | Material | Theoretical Amount (g) |
|---|---|---|
| 1.2% | Epinephrine Bitartrate | 2.183 |
| | Trehalose | 97.817 |
| 4% | Epinephrine Bitartrate | 7.277 |
| | Trehalose | 92.723 |
| 12% | Epinephrine Bitartrate | 21.831 |
| | Trehalose | 78.169 |

TABLE 5

Actual inhalable epinephrine composition with trehalose as carrier.

| Blend Code | Epinephrine (% w/w) | Material | Actual Amount (g) |
|---|---|---|---|
| 3A | 12% | Epinephrine Bitartrate | 2.85* |
| | | Trehalose | 10.15 |

*The target drug substance mass of 2.838 g was adjusted to 2.85 g to account for epinephrine potency of the specific lot of epinephrine bitartrate drug substance used in the experiment.

Upon achieving acceptable blending, the formulations were further processed by filling in to glass vials for stability testing. No issues were encountered in performing the powder handling transfers from bulk blend to filled vials.

Example 4: Manufacturing Process

Step 1: Micronizing of API (Epinephrine Bitartrate)

Epinephrine bitartrate drug substance (API) was procured from Transo-Pharm Handels-GmbH (Siek, Germany). Micronization of epinephrine bitartrate (API) was performed using an air jet micronizer (MC Jetmill type 50) and a dosing feeder (K-Tron T20) to deliver the epinephrine bitartrate to the feed chute at a controlled flow rate.

The API was micronized using the following milling process parameters and scale, and achieved the listed yields as shown in table 6:

TABLE 6

Micronization process parameters, scale and output yield.

| Batch Number | Feed Rate (g/min) | Pressure (bar) | Temperature (° C.) | Scale (g) | Yield (g) | Yield (%) |
|---|---|---|---|---|---|---|
| E80-18002M1 | 10.0 | 12.0 | −30 | 50.00 | 37.00 | 78.00 |
| E80-18002M2 | 10.0 | 12.0 | RT | 47.00 | 39.70 | 86.60 |
| 160916M2 | 10.0 | 10.5 | RT | 295.2 | 264.6 | 91.33 |

Cryogenic micronization using a temperature controlled variable feed system delivering a liquid nitrogen co-feed to the jet mill was used to micronize API in batch E80-18002M1 and provided for a similarly useful milling process and subsequent formulated inhalable epinephrine blend. Cryogenic micronization was found to be a suitable alternative processing mode of operating the jet mill. Nevertheless, the ambient room temperature (RT) conventional jet milling configuration, without the cryogenic feed system, was also found to be a suitable process for producing inhalable crystalline micronized epinephrine bitartrate and a simpler process configuration. The powders from either processing configuration yielded materials that exhibited distinct X-ray powder diffraction peaks characteristic of epinephrine bitartrate and without substantial evidence of amorphization (loss of crystallinity). Therefore the micronization process is surprisingly versatile being able to deliver a crystalline powder post milling, whether or not the temperature during milling is uncontrolled ambient, or whether it is controlled to cryogenic low temperature conditions. Since some API materials undergo a substantial extent of amorphization during air jet milling (micronization), cryogenic milling is sometimes an essential more complex processing configuration to produce an inhalable drug substance powder without loss of crystallinity. Epinephrine bitartrate was surprisingly found to not necessarily require this, giving a simpler process option with versatility to operate at ambient or colder temperatures where desired.

The powders pre and post micronization were analyzed for particle size using a laser diffraction system in dry powder sample preparation mode (Sympatec Helos, Clausthal-Zellerfeld, Germany). From the particle size analyses, the data for volume based mean particle size (Dv50), the cumulative 90% of volume size (Dv90), and the total volume of particles with size below 5 μm values are summarised in Table 7.

TABLE 7

Micronization results.

| Customer Batch Number | Sample | Dv50 (μm) | Dv90 (μm) | Volume below 5 μm (%) |
|---|---|---|---|---|
| E80-18002 | Unmicronised | 37.50 | 193.89 | 8.18 |
| E80-18002M1 | Trial 1 | 1.62 | 3.23 | 99.52 |
| | Drum 1 | 1.65 | 3.55 | 98.39 |
| E80-18002M2 | Trial 1 | 1.57 | 3.38 | 98.91 |
| | Drum 1 | 1.52 | 3.25 | 99.20 |
| 160916M2 | Trial 1 | 1.83 | 3.76 | 97.77 |
| | Drum 1 bottom | 1.77 | 3.65 | 98.37 |
| | Drum 1 top | 1.83 | 3.71 | 98.27 |
| | Final Sample | 1.79 | 3.65 | 98.42 |

Crystalline epinephrine bitartrate was found to micronize in a robust manner in scales ranging from 50 g to 300 g. For powders to impact and deposit in the deep lung, it is generally accepted that the portion of particles in the 0.5-5 μm size range are particularly suitable for this. Larger diameter particles may impact the throat or upper airways, and finer particles may to some extent be exhaled. Therefore, the particle size analysis data indicates that micronization via conventional ambient (RT) or cryogenic milling conditions is useful to convert the procured epinephrine bitartrate from an essentially non-deliverable state via the lung, into a bulk drug substance of epinephrine bitartrate that is essentially less than 5 μm and where the mean size is within the desired 0.5-5 μm size range. Therefore micronization is useful for processing epinephrine for inhaled drug delivery, without loss of crystallinity.

Step 2: Low Shear Mixing of Epinephrine Bitartrate and Lactose Monohydrate

Prior to blending, the micronized epinephrine bitartrate was passed through a 250 μm mesh sieve to eliminate any level of agglomeration, if present.

The first blending step involved mixing the epinephrine bitartrate with an equivalent amount of lactose monohydrate and this mixture was blended in a Turbula mixer at approximately 34 rpm for approximately 30 mins.

The remainder of the lactose monohydrate required for the formulation was split into three equivalent amounts.

Three additional blending steps were performed by mixing one third of the remaining lactose monohydrate into the powder bulk, followed by blending in a Turbula mixer at approximately 34 rpm for approximately 30 mins.

After resting, the final formulation was passed through a 250 μm mesh sieve twice before being returned to the blending vessel. The formulation was manually rotated before sampling.

Blend uniformity testing results of the 1.2% (Blend Code 1B) and 6% (Blend Code 1D) formulations are summarised in Table 8.

TABLE 8

Crystalline micronized blended epinephrine blend uniformity testing results, tested by representative sampling and HPLC analysis (n = 10).

| Blend Code | Epinephrine (% w/w) | Assay Mean (% w/w) | Uniformity of the Blend % Relative Standard Deviation (% RSD) |
|---|---|---|---|
| 1B | 1.2 | 1.2 | 2.3 |
| 1D | 6 | 6.2 | 1.6 |

The formulation blend exhibited a high degree of blend uniformity and expected assay (potency). The bulk powder was further processed via accurate weight based filling into capsules and packaged into sealed glass jars without a desiccant. Sample capsules from each lot containing 25 mg of blend were loaded into a Plastiape RS01 dry powder inhaler device with a shortened mouthpiece and tested using a Next Generation Impactor (NGI). The aerosol was characterized for aerodynamic particle size distribution (APSD), summarised in Table 9.

TABLE 9

Aerodynamic particle size data of crystalline micronized lactose blended epinephrine bitartrate (NGI results).

| Blend Code | Epinephrine (mg) per 25 mg Capsule | Epinephrine (% w/w) | MMAD (μm) | FPF[a] (%) | FPD <5 μm (mg) |
|---|---|---|---|---|---|
| 1B | 0.3 | 1.2 | 2.4 | 45.25 | 0.11 |
| 1D | 1.5 | 6 | 3.1 | 40.67 | 0.43 |

[a]Fine Particle Fraction (FPF) expressed as a percentage of the fine particle dose relative to the emitted dose.

This APSD data indicates the blend performed surprisingly well in the RS01 device. The mass mean aerodynamic diameter (MMAD) was found to be well within the desired 0.5-5 μm range. The fine particle fraction (FPF) was observed to be significantly higher than the typical range of approximately 25-30% often observed for DPI devices, which suggests the crystalline micronized epinephrine bitartrate particles were efficiently deagglomerated from the carrier lactose particles during the aerosolization. Therefore, useful fine particle doses (FPD) were observed indicating a substantial quantity of the capsule drug content would be delivered to the deep lung of a patient in need of epinephrine. For reference intramuscular administration of epinephrine via autoinjector to an adult anaphylaxis patient is prescribed at 0.3 mg per injection. Therefore the blends prepared in this example achieved inhalation delivery fine particle doses (FPD) by NGI testing that bracket this useful therapeutic drug dose level (0.11-0.43 mg epinephrine).

A 6 month timepoint study was performed on an epinephrine bitartrate and lactose monohydrate formulation (Blend Code 8B) with an epinephrine potency of 12% w/w. The results of Next Generation Impactor testing at each time point after being held at 25° C./60% RH are summarised in Table 10.

TABLE 10

Next Generation Impactor results for 12% w/w epinephrine blend (Blend Code 8B).

| Timepoint | MMAD (μm) | FPD <5 μm (mg) | FPF (%) |
|---|---|---|---|
| Initial | 3.6 | 0.62 | 25.98 |
| 1 month | 3.7 | 0.55 | 22.67 |
| 3 month | 3.7 | 0.51 | 21.31 |
| 6 month | 4.4 | 0.42 | 17.71 |

Results of Next Generation Impactor testing over 6 months storage show consistent key parameters for inhalation delivery including the desired MMAD range and FPD levels higher than the expected minimum necessary for treating a patient in need via inhalation, and without use of an intramuscular injection.

OR Step 2: High Shear Mixing of Epinephrine Bitartrate and Lactose Monohydrate

Epinephrine bitartrate was passed through a 250 μm mesh sieve to eliminate any level of agglomeration, if present.

A quantity of epinephrine bitartrate equivalent to 5.2% w/w epinephrine was added to a Diosna P1-6 (Germany) high shear mixer bowl with alpha-lactose monohydrate, layering the active ingredient between equal portions of the lactose.

The manufacturing and sampling parameters listed in Table 11 were used in a successive manner for blending the remaining blend from the respective previous run.

TABLE 11

Manufacturing and sampling parameters for high shear blending of crystalline epinephrine bitartrate with alpha-lactose monohydrate.

| Run Number | Impeller Speed (RPM) | Granulator Speed (RPM) | Time for Sampling |
|---|---|---|---|
| 1 | 150 | 0 | 2 minutes |
| | | | 15 minutes |
| | | | 30 minutes |
| 2 | 300 | 0 | 15 minutes |
| | | | 30 minutes |
| 3 | 600 | 0 | 15 minutes |
| | | | 30 minutes |

Following mixing, powder samples were taken representatively from various locations in the mixing bowl and tested by HPLC for blend uniformity. Additional blend uniformity testing was performed following a 4 day and 7 day resting period. The uniformity results are summarised in Table 12.

TABLE 12

Epinephrine blend uniformity testing results following high shear mixing

| Resting Period | Run | Blending Time (mins) | Assay Mean (% w/w) | % RSD |
|---|---|---|---|---|
| Day 0 | 1 | 2 | 5.2 | 3.9 |
| | | 15 | 5.2 | 5.2 |
| | | 30 | 5.1 | 15.9 |
| | 2 | 15 | 5.0 | 11.9 |
| | | 30 | 5.1 | 8.8 |
| | | 30 | 5.2 | 6.3 |
| | 3 | 15 | 5.2 | 6.4 |
| | | 30 | 5.1 | 4.7 |
| Day 4 | 1 | 30 | 5.1 | 4.6 |
| | 2 | 30 | 5.3 | 7.0 |
| | 3 | 30 | 5.3 | 3.4 |
| Day 7 | 1 | 30 | 5.1 | 2.7 |
| | 2 | 30 | 5.2 | 4.4 |

TABLE 12-continued

Epinephrine blend uniformity testing results following high shear mixing

| Resting Period | Run | Blending Time (mins) | Assay Mean (% w/w) | % RSD |
|---|---|---|---|---|
| | 3 | 30 | 5.1 | 3.2 |

The formulation blends for Run 1 and Run 3 were further processed by accurately filling into capsules at 25 mg fill mass target, then loaded into a Plastiape RS01 dry powder inhaler device with a shortened mouthpiece and tested using a Next Generation Impactor. The results are summarised in Table 13.

TABLE 13

Next Generation Impactor results.

| Run | MMAD (μm) | FPD <5 μm (mg) | FPF[a] (%) |
|---|---|---|---|
| 1 | 2.65 | 0.38 | 41.84 |
| 3 | 2.66 | 0.39 | 44.77 |

[a]Fine Particle Fraction (FPF) expressed as a percentage of the fine particle dose relative to the emitted dose.

Results of Next Generation Impactor testing of impeller speeds from 150 RPM to 600 RPM show consistent key parameters for inhalation delivery with MMAD in the desired 1-5 μm range for delivery to the deep lung, and with fine particle dose very close to and slightly higher than the 0.3 mg prescribed dose for autoinjector intramuscular delivery of epinephrine to a patient suffering anaphylaxis and in need of epinephrine.

This data also demonstrates that crystalline micronized epinephrine bitartrate formulated with lactose can be efficiently mixed by either low shear or high shear blending methods (for example the use of Turbula and Diosna equipment here, or other similar mixing machine brands and types). In some cases a high shear mixing process may be more readily scaled up to a larger batch size, and in other cases, small scale lots are more convenient to blend via low shear methods. The data surprisingly shows that crystalline micronized epinephrine bitartrate can be blended in a robust processing manner regardless of the type of mixing equipment's (level of shear force). Further the APSD data verifies that useful MMAD and FPD performance characteristics were observed regardless of the type of mixing technology applied.

Example 5: Agglomeration Experiments With Epinephrine Bitartrate and Magnesium Stearate Particle size distribution was analysed at different time points on the micronized epinephrine bitartrate alone. The results comparing the initial testing time point to the 4 week time point are summarised in Table 14.

TABLE 14

Particle size distribution of micronized epinephrine bitartrate.

| Time Point | Dv10 (μm) | Dv50 (μm) | Dv90 (μm) | Volume below 10 μm (%) |
|---|---|---|---|---|
| Initial | 0.310 | 1.73 | 57.8 | 79.94 |
| 4 weeks (2-8° C.) | 3.49 | 248 | 847 | 22.62 |
| 4 weeks (40° C./75% RH) | 2.40 | 294 | 1200 | 30.53 |

Figure 2:
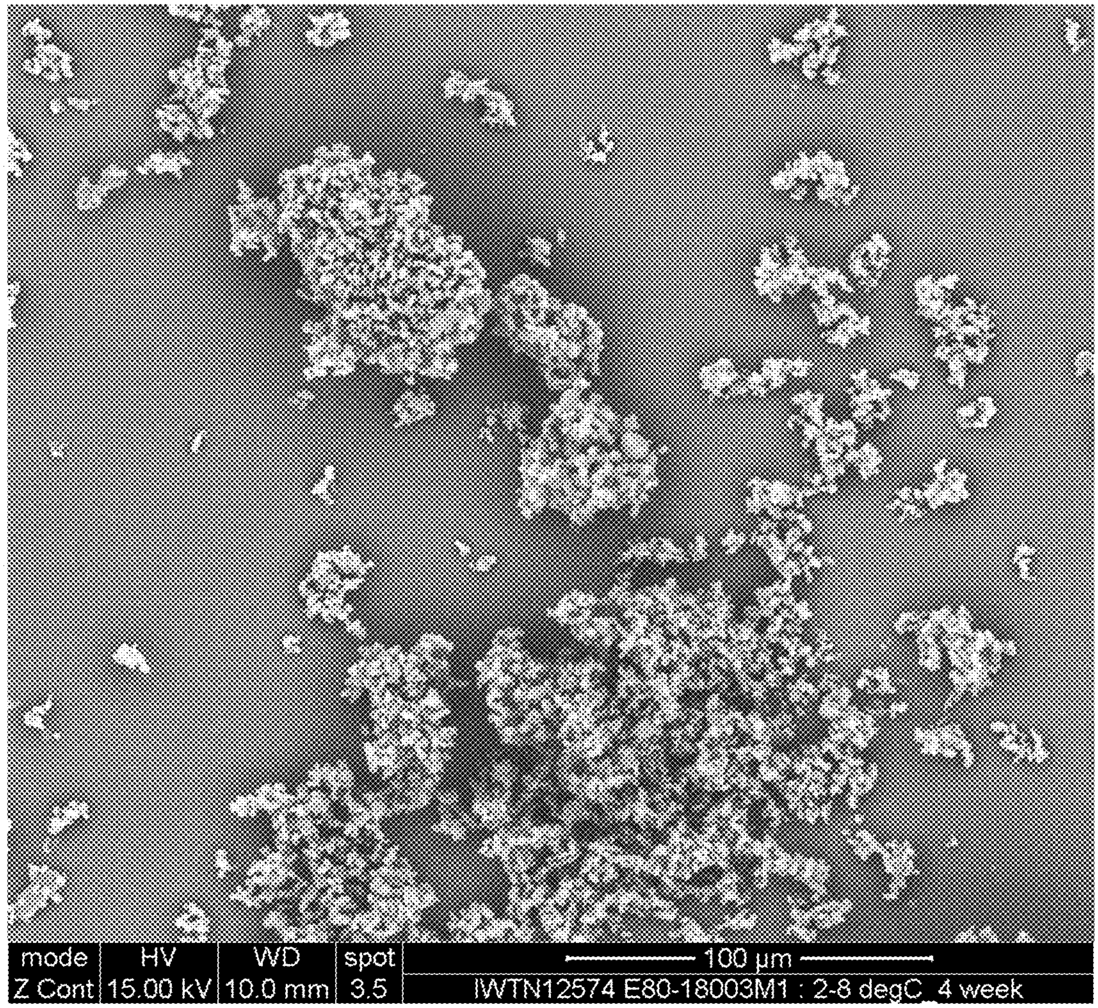
FIG. 2: shows a SEM image of the particle size distribution of micronized epinephrine bitartrate at the 4 week time point (2-8° C.).
Figure 3:
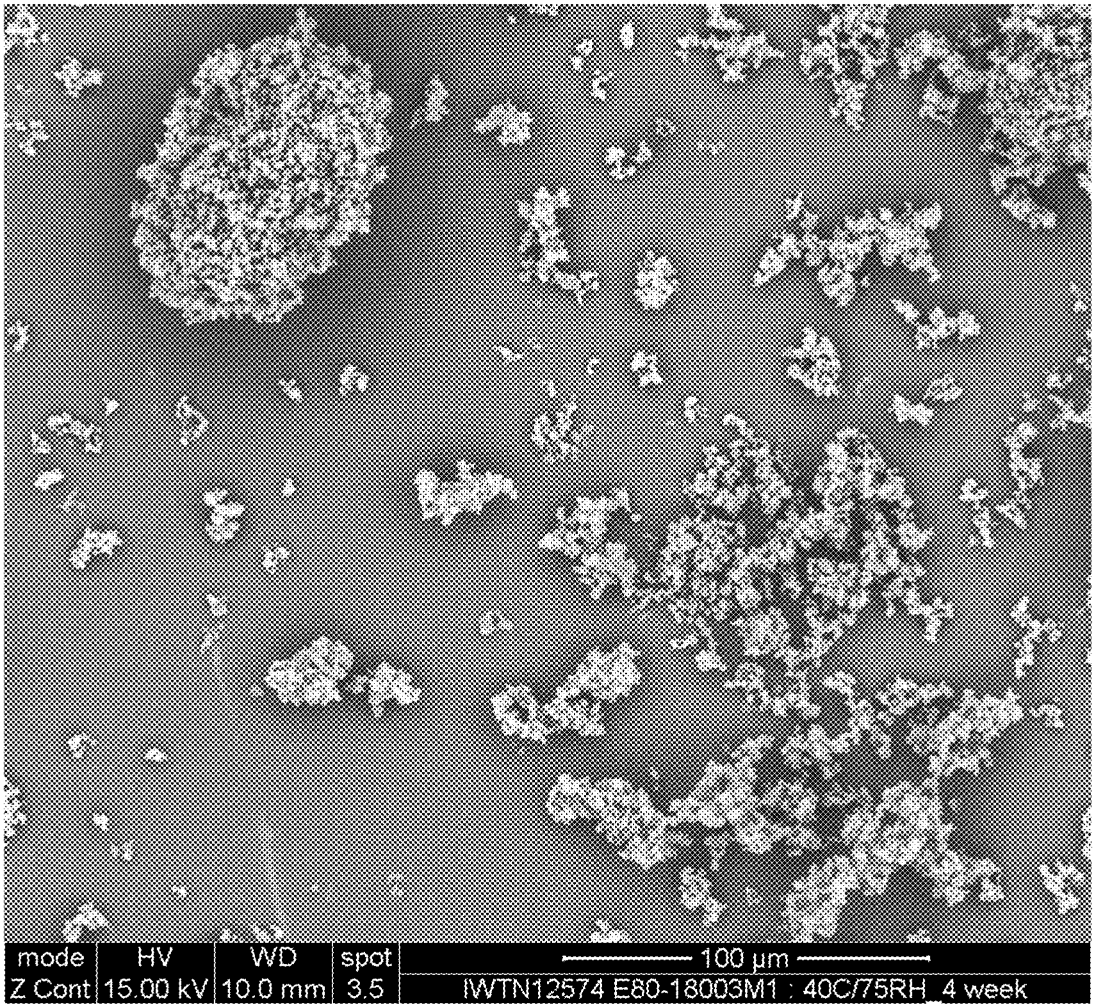
FIG. 3: shows a SEM image of the particle size distribution of micronized epinephrine bitartrate at the 4 week time point (40° C./75% RH).

FIGS. 1 to 3 show scanning electron microscope images corresponding to the three time points in Table 14.

Based on the profound increase in all particle size parameters and the decrease in the proportion of the particles below 10 μm, it is obvious that the crystalline micronized epinephrine bitartrate alone, without the addition of lactose monohydrate as a carrier, naturally tends to agglomerate. This extent of agglomeration is overly high for a DPI product since the proportion of the drug available to be delivered to the deep lung would be substantially reduced potentially to sub-therapeutic dosing levels due to the agglomeration.

The particle size distribution was analysed at different time points on the crystalline micronized epinephrine bitartrate with the addition of magnesium stearate (MgSt). The results comparing the initial testing time point to the 4 week timepoint are summarised in Table 15.

TABLE 15

Particle size distribution of micronized epinephrine bitartrate and MgSt.

| Time Point | Dv10 (μm) | Dv50 (μm) | Dv90 (μm) | Volume below 10 μm (%) |
|---|---|---|---|---|
| Initial | 0.265 | 1.15 | 4.2 | 94.88 |
| 4 weeks (2-8° C.) | 0.952 | 95.1 | 524 | 33.78 |
| 4 weeks (40° C./75% RH) | 8.07 | 181 | 434 | 10.82 |

Figure 4:
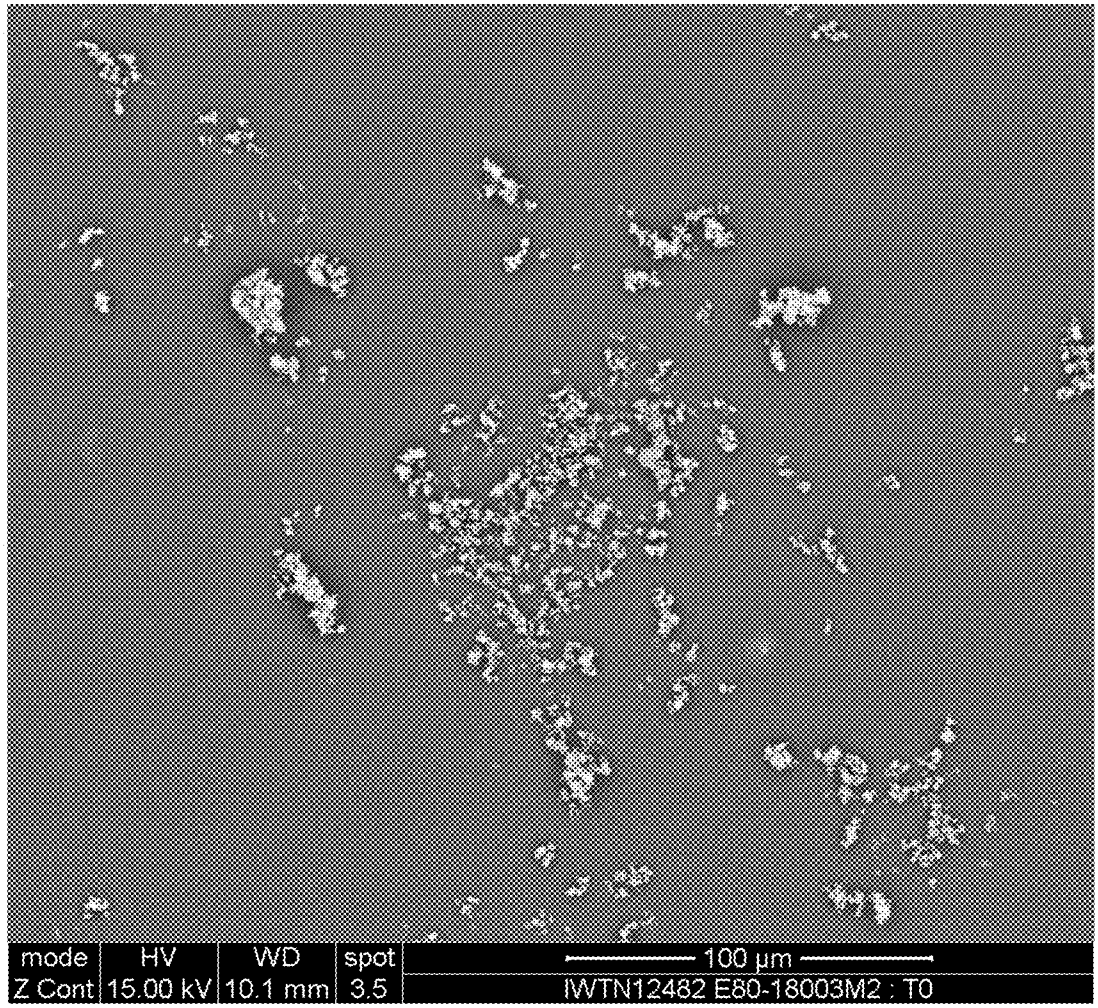
FIG. 4: shows a SEM image of the particle size distribution of micronized epinephrine bitartrate and magnesium stearate at an initial time point.
Figure 5:
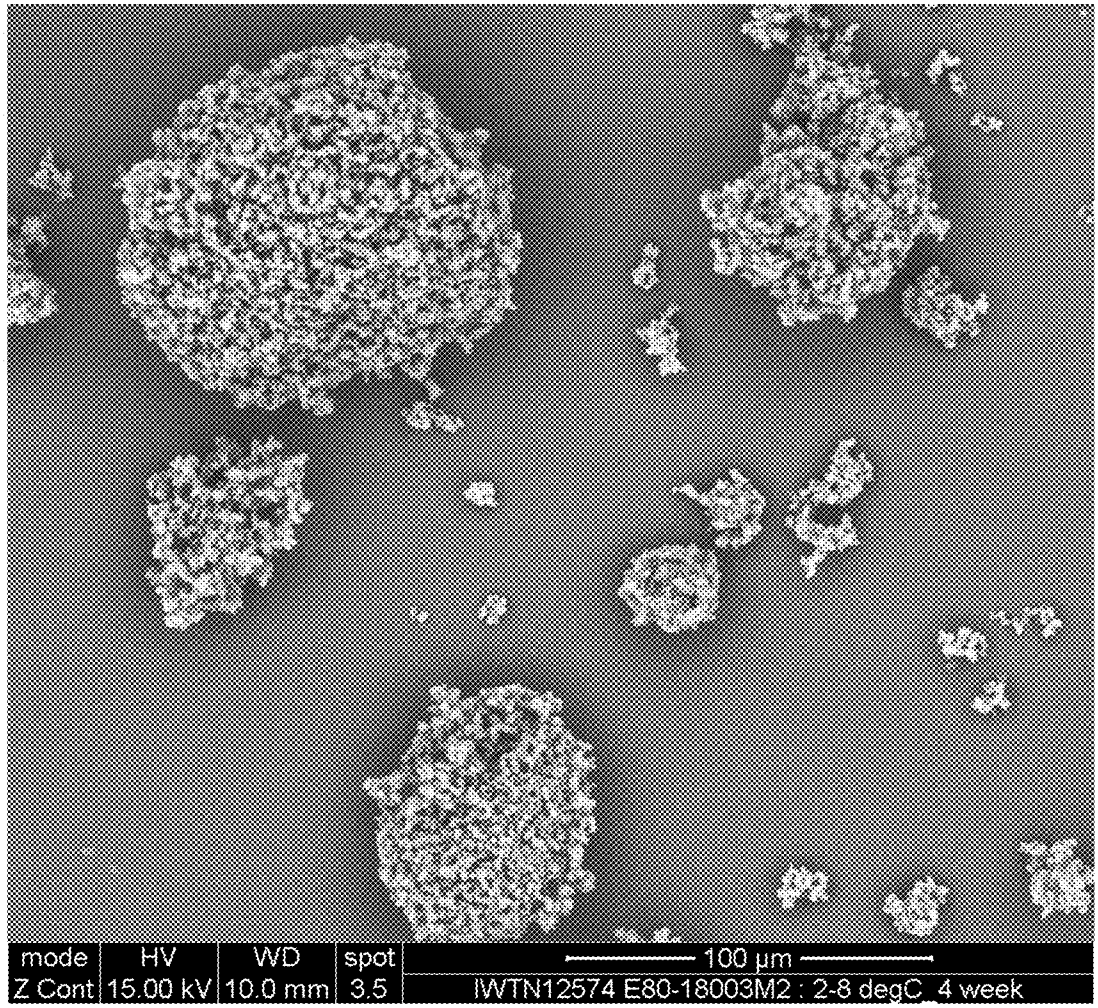
FIG. 5: shows a SEM image of the particle size distribution of micronized epinephrine bitartrate and magnesium stearate at the 4 week time point (2-8° C.).
Figure 6:
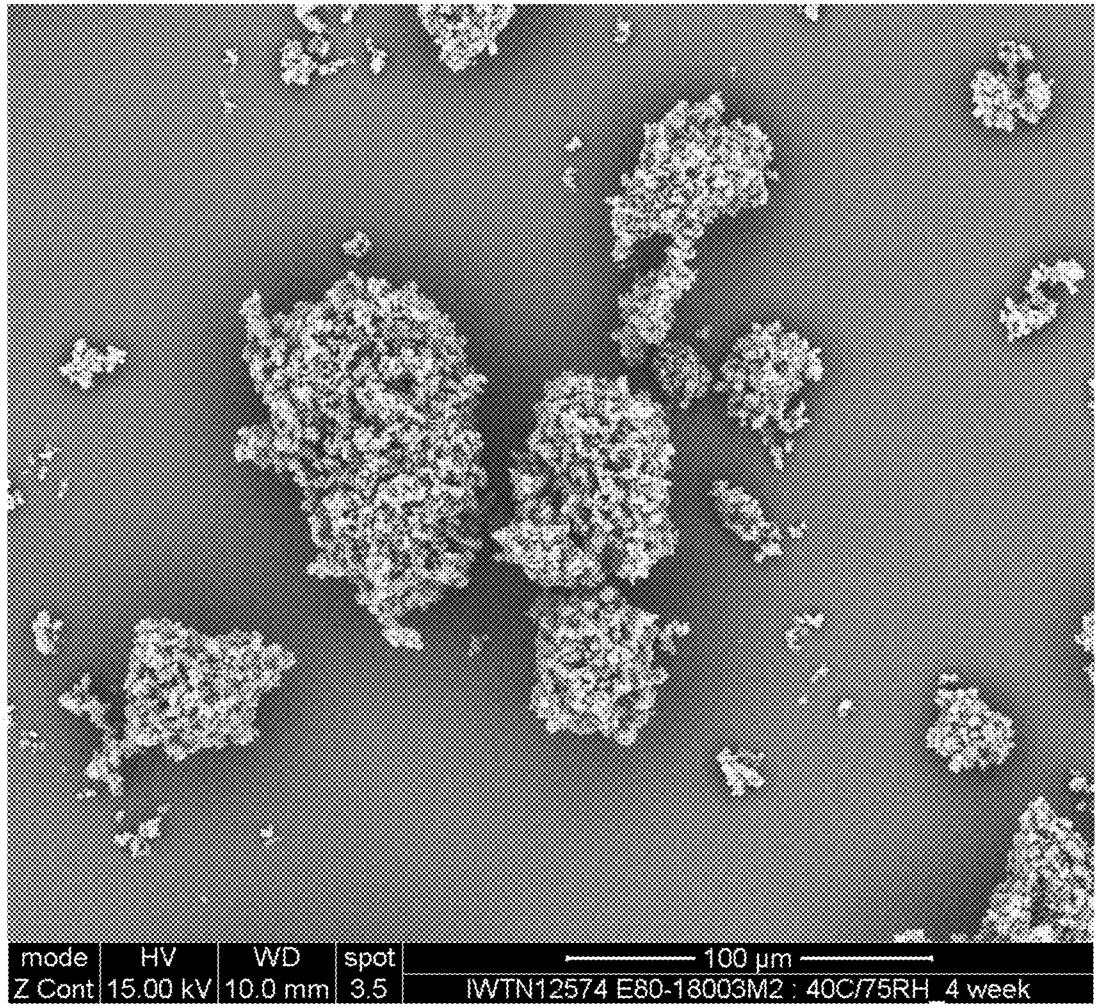
FIG. 6: shows a SEM image of the particle size distribution of micronized epinephrine bitartrate and magnesium stearate at the 4 week time point (40° C./75% RH).

FIGS. 4 to 6 show scanning electron microscope images corresponding to the three time points in Table 15.

Magnesium stearate is commonly used as a lubricant excipient or force control agent in DPI formulations to assist in breaking up inter-particle and particle/surface attractive forces allowing a better dispersion of fine drug particles. It is clear from the results in table 15 that the formulation with magnesium stearate still tends to agglomerate even though it might be expected in the art that magnesium stearate would be a useful functional excipient for avoiding or minimizing agglomeration.

Example 6: Agglomeration Experiments With the Addition of Lactose Monohydrate

TABLE 16

Crystalline micronized epinephrine bitartrate formulation with alpha-lactose monohydrate as carrier.

| Formulation | Drug Amount (g) | Carrier | Magnesium Stearate Content (g) | Scale (g) |
|---|---|---|---|---|
| 1 | 0.2 | Lactose Monohydrate | — | 2 |
| 2 | 0.2 | Lactose Monohydrate | 0.04 | 2 |

The formulations were manufactured with alpha-lactose monohydrate in a 10% w/w API loading with micronized crystalline epinephrine bitartrate material. Prior to blending, the API was passed through a 250 μm sieve using a pallet knife with moderate manual force to assist the powder passing the screen. No large particles remained on the sieve mesh post-sieving. The blends were then produced by layering the API with the excipient carrier and magnesium stearate, where appropriate, in a glass vial and mixing by Turbula for approximately 30 min at approximately 34 rpm.

Figure 7:
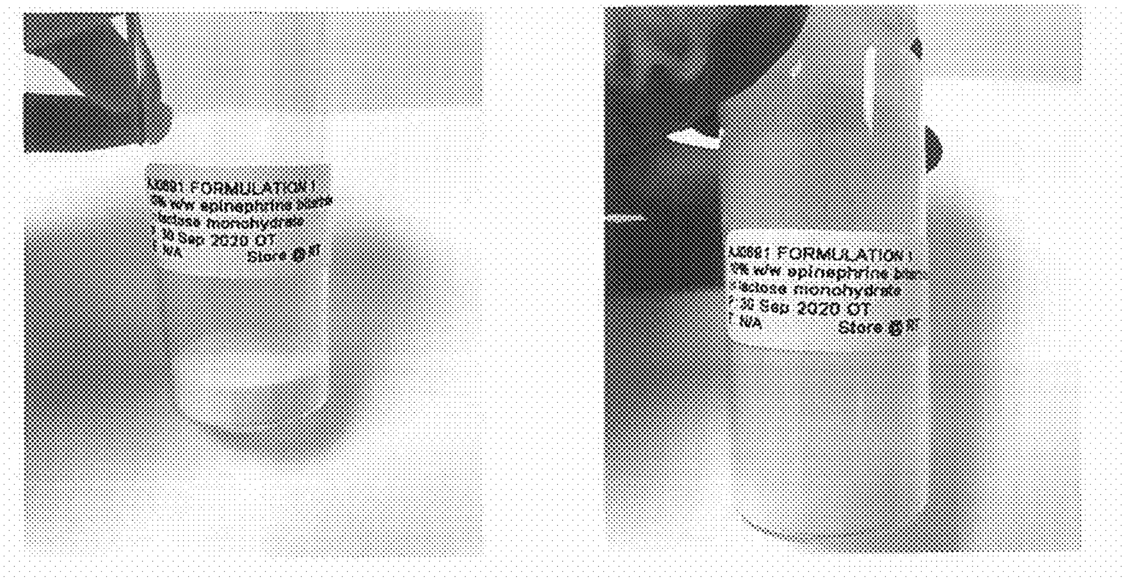
FIG. 7: (A. Epinephrine formulation, pre-blending; B. Epinephrine formulation, post-blending) shows that the epinephrine formulation with lactose monohydrate pre- and post-blending is free from loose agglomerates.
Figure 8:
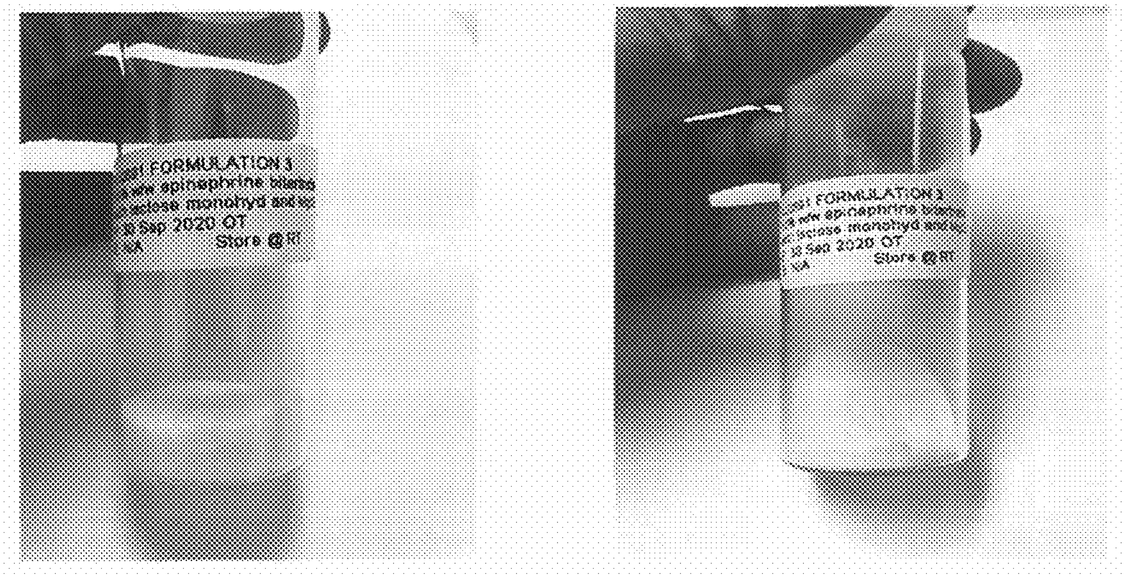
FIG. 8: (A. Epinephrine formulation, pre-blending, +MgSt; B. Epinephrine formulation, post-blending, +MgSt) shows that the epinephrine formulation with lactose monohydrate and magnesium stearate pre- and immediately post-blending is free from loose agglomerates.

FIGS. 7 (A. Epinephrine formulation, pre-blending; B. Epinephrine formulation, post-blending) and 8 (A. Epinephrine formulation, pre-blending, +MgSt; B. Epinephrine formulation, post-blending, +MgSt) show that both formulations of table 16 pre- and immediately post-mixing are free from loose agglomerates.

Example 7a: High Chemical and Physical Stability of Formulation

A 6 month duration stability study was performed on an epinephrine bitartrate and lactose monohydrate formulation (Blend Code 8B) with an epinephrine blend potency of 12% w/w. The results of stability testing at each time point after being held at 25° C./60% RH are summarised in Table 17. Note at 25 mg per capsule blend fill weight target, this corresponds to 3.0 mg epinephrine strength per capsule.

TABLE 17

Summary of 6 months chemical and physical stability data of an epinephrine bitartrate and lactose monohydrate formulation (Blend Code 8B) stored at RH 25 C./60% RH.

| | | Test | | | | | | | |
|---|---|---|---|---|---|---|---|---|---|
| | | Initial | | 1 month | | 3 month | | 6 month | |
| Assay (n = 2) mg/capsule | | 3.0 | | 3.1 | | 3.2 | | 3.0 | |
| Related | | RT | % | RT | % | RT | % | RT | % |
| Substances | Imp A | 3.16 | 0.12 | 3.28 | 0.13 | 3.18 | 0.12 | 3.29 | 0.06 |
| (n = 2) | Imp B | | | | | 0.85 | 0.06 | 0.85 | <0.05 |
| (% impurity) | Imp D | | | | | 3.32 | <0.05 | | |
| Mean FPD (mg) (≤5 μm) (n = 3) | | 0.62 | | 0.55 | | 0.51 | | 0.42 | |
| Mean FPF (FPD as % total dose) ≤5 μm (n = 3) | | 25.98 | | 22.67 | | 21.31 | | 17.71 | |
| Mean MMAD (μm) (n = 3) | | 3.6 | | 3.7 | | 3.7 | | 4.4 | |
| Mean GSD (n = 3) | | 1.7 | | 1.7 | | 1.7 | | 1.8 | |
| Mean Total Delivered | | 30 L/min | 2.00 | 30 L/min | 2.17 | 30 L/min | 2.11 | 30 L/min | 2.08 |
| Dose (n = 10) (mg) | | 60 L/min | 2.26 | 60 L/min | 2.23 | 60 L/min | 2.33 | 60 L/min | 2.21 |
| | | 90 L/min | 2.22 | 90 L/min | 2.01 | 90 L/min | 2.28 | 90 L/min | 2.37 |
| Water content (n = 3) (%) | | 4.15 | | 4.10 | | 4.04 | | 3.98 | |

RT—retention time on the HPLC chromatograph used for analysis of impurities, FPD—Fine Particle Dose, FPF—Fine Particle Fraction, MMAD—Mass Median Aerodynamic Diameter, GSD—Geometric Standard Deviation; Related Substances impurities have a limit of quantification of 0.05%; Testing was performed with a Plastiape RS01 that was modified to have a shorter mouthpiece.

Example 7a demonstrated that a representative blend of epinephrine bitartrate blended with alpha-lactose monohydrate exhibited high chemical stability over the 6 month period of storage and testing at 25° C. and 60% relative humidity, which is the storage condition used to simulate controlled room temperature stored pharmaceutical products. There was no significant change in assay from the 3.0 mg/capsule initial state. The impurity profile assessed by HPLC analysis with a limit of quantitation of 0.05% indicated that no impurities grew significantly over the 6 months of storage, with impurity A remaining at a similar level over the 6 months, without any significant growth over time on storage. Impurity B was detected at about the limit of quantitation at 3 months and again numerically at 0.03% at the 6 month time point, but at that trace level, the quantity was less than the limit of quantitation. The water content did not exhibit significant change over the 6 months period, and the majority of the water mass quantified corresponds to the weight of the monohydrate water in the lactose excipient. This suggests there was no significant moisture uptake or loss in the blend over the 6 month storage period. Therefore, the encapsulated blend of crystalline micronized epinephrine bitartrate with alpha-lactose monohydrate exhibited highly stable chemical properties over 6 months of stability storage and supportive of a convenient room temperature stored pharmaceutical product. Further, Example 7a demonstrated that a representative blend of epinephrine bitartrate blended with alpha-lactose monohydrate exhibited high physical stability over the 6 month period of storage and testing at 25° C. and 60% room humidity, which is the storage condition used to simulate controlled room temperature stored pharmaceutical products. The aerosol performance properties tested indicated acceptable and useful mean total delivered dose of epinephrine across a wide range of inspiratory flow rates (tested by Next Generation Impactor, NGI and with an RS01 Plastiape DPI high resistance modified device). The mass mean aerodynamic diameter (MMAD) remained below the 5 micron threshold and with consistently low variability (GSD) supporting delivery to the deep lung of crystalline micronized epinephrine bitartrate from the lactose blend throughout the storage testing period. Therefore, the encapsulated blend of crystalline micronized epinephrine bitartrate with alpha-lactose monohydrate exhibited highly stable physical properties over 6 months of stability storage and supportive of a convenient room temperature stored dry powder inhalation delivered pharmaceutical product.

Example 7b: High Chemical and Physical Stability of Formulation

Similarly to Example 7a, Blend Code 1C was processed and then accurately filled into Size 3 HPMC capsules in an equivalent manner to Example 4 Step 2. The capsules were packaged into HDPE bottles with desiccant and stored for 6 months at 25° C./60% RH and 40° C./75% RH.

The results of stability testing at each time point after being held at 25° C./60% RH are summarised in Table 18. Note at 25 mg per capsule blend fill weight target, this corresponds to 1.0 mg epinephrine strength per capsule.

TABLE 18

Summary of 6 months chemical and physical stability data of an epinephrine bitartrate and lactose monohydrate formulation (Blend Code 1C) stored at 25° C./60% RH.

| | Test | | | |
|---|---|---|---|---|
| | Initial | 1 month | 3 month | 6 month |
| Assay (n = 2) (%) | 95 | 96 | 98 | 97 |
| Related Substances (n = 2) Impurity B (%) | <0.2 | <0.2 | 0.20 | <0.2 |
| Mean FPD (mg) (≤5 μm) (n = 3) | 0.28 | 0.28 | 0.28 | 0.32 |
| Mean FPF (FPD as %) ≤5 μm (n = 3) | 44 | 46 | 44 | 52 |
| Mean MMAD (μm) (n = 3) | 2 | 2 | 2 | 2 |
| Mean Metered Dose (n = 10) (% LC) | 92 | 94 | 95 | 95 |
| Water content (n = 3) (%) | 4.8 | 4.9 | 4.8 | 4.9 |

FPD—Fine Particle Dose, FPF—Fine Particle Fraction expressed as a percentage of the fine particle dose relative to the emitted dose, MMAD—Mass Median Aerodynamic Diameter, Related Substances impurities have a limit of quantification of 0.05%, the following Related Substances were within the specified acceptance criteria: Impurity A—<0.3, Impurity C—<0.2, Impurity D—<0.1, Impurity E—<0.1, Each Unspecified Impurity—<0.5; Impurity B was the only impurity that was detected and quantified across the testing time points; Testing was performed with a Plastiape RS01 that was modified to have a shorter mouthpiece.

The results of stability testing at each time point after being held at 40° C./75% RH are summarised in Table 19. Note at 25 mg per capsule blend fill weight target, this corresponds to 1.0 mg epinephrine strength per capsule.

TABLE 19

Summary of 6 months chemical and physical stability data of an epinephrine bitartrate and lactose monohydrate formulation (Blend Code 1C) stored at 40° C./75% RH.

| | Test | | | |
|---|---|---|---|---|
| | Initial | 1 month | 3 month | 6 month |
| Assay (n = 2) (%) | 95 | 96 | 99 | 97 |
| Related Substances (n = 2) Impurity B (%) | <0.2 | <0.2 | <0.2 | 0.31 |
| Mean FPD (mg) (≤5 μm) (n = 3) | 0.28 | 0.34 | 0.29 | 0.34 |
| Mean FPF (FPD as %) ≤5 μm (n = 3) | 44 | 48 | 45 | 49 |
| Mean MMAD (μm) (n = 3) | 2 | 2 | 2 | 2 |
| Mean Metered Dose (n = 10) (% LC) | 92 | 94 | 96 | 95 |
| Water content (n = 3) (%) | 4.8 | 4.9 | 4.9 | 4.8 |

FPD—Fine Particle Dose, FPF—Fine Particle Fraction expressed as a percentage of the fine particle dose relative to the emitted dose, MMAD—Mass Median Aerodynamic Diameter, Related Substances impurities have a limit of quantification of 0.05%, the following Related Substances were within the specified acceptance criteria: Impurity A—<0.3, Impurity C—<0.2, Impurity D—<0.1, Impurity E—<0.1, Each Unspecified Impurity - <0.5; Impurity B was the only impurity that was detected and quantified across the testing time points; Testing was performed with a Plastiape RS01 that was modified to have a shorter mouthpiece.

Example 7b demonstrates similarly useful stability results for a 1.0 mg strength capsule. Further packaging in HDPE bottles with desiccant corresponded to superior stability properties at real time and accelerated storage conditions.

Example 8: Addition of Lactose Fines

During the 6 month stability study in Example 7, additional formulations were blended to assess how the inclusion of fine alpha-lactose monohydrate carrier particles would affect the stability and performance of the formulation stored at 25° C./60% RH.

Respitose SV003 was used as the coarse lactose carrier, and Lactohale LH300 was used as the fine lactose carrier particles. Both fine and coarse lactose materials were alpha-lactose monohydrate. Different ratios of lactose fines were mixed with either the standard crystalline micronized epinephrine bitartrate or cryogenically micronized epinephrine bitartrate as summarised in Table 20.

TABLE 20

Formulations with coarse lactose and lactose fines.

| Blend Code | Formulation | API | API*(% w/w) | Coarse Carrier (% w/w) | Fine Carrier (% w/w) |
|---|---|---|---|---|---|
| 8A | A | E80-18002M1 (Cryo milled) | 22.4 | 77.6 | 0 |
| 8B | B | E80-18002M2 (Standard Milled) | 22.4 | 77.6 | 0 |
| 8C | C | E80-18002M2 (Standard Milled) | 22.4 | 74.6 | 3 |
| 8D | D | E80-18002M2 (Standard Milled) | 22.4 | 67.6 | 10 |
| 8E | E | E80-18002M1 (Cryo milled) | 22.4 | 74.6 | 3 |

*adjusted for purity and salt/base conversion to achieve an epinephrine blend potency of 12% w/w Assay results were as expected for all formulations and were consistent with the previous time points verifying the product potency was stable across the storage period regardless of the presence of lactose fines or the ratio of fines to coarse lactose materials in the blends.

The MMAD for all formulations plateaued after the one month time point, apart from Formulation B which had increased slightly. For Formulation A the FPD stayed relatively consistent after the 3 month time point, and the % FPF appeared to have stabilised at the 1 month time point. For Formulation B, the FPD and % FPF decreased with each subsequent time point. For Formulation C the FPD at the 6 month time point was consistent with the previous time point. The % FPF increased slightly since the 3 month time point. For Formulation E, the FPD had increased since the 3 month time point, and was higher than the initial time point. The % FPF remained relatively consistent across all time points.

Formulation A showed the highest proportion of deposition with particles in the 0-3 μm, with a distribution indicative of deep lung delivery.

The delivered dose results at the 6 month time point for all formulations were consistent with the initial time point. Water content was around 4% for all formulations, which was consistent with the previous time points. The % RSD was low for all formulations.

Example 9: Stability of Epinephrine Bitartrate+α-Lactose Monohydrate Formulation vs Epinephrine Bitartrate+α-Lactose Monohydrate+Magnesium Stearate Formulation A composition of epinephrine bitartrate+α-lactose monohydrate, only, demonstrated significantly superior chemical stability over an epinephrine bitartrate+α-lactose monohydrate+magnesium stearate formulation as is demonstrated in tables 21 and 22, below. This is surprising since, based on the lack of stability and the significant agglomeration observed with the epinephrine bitartrate alone, it was expected that the addition of magnesium stearate would be required to achieve the necessary stability for storage. The sum of related substances developing over a period of 1 month of stressed storage shows minimum increase for epinephrine bitartrate+α-lactose monohydrate. Meanwhile, for the epinephrine bitartrate+α-lactose monohydrate+magnesium stearate formulation, the related substances increased dramatically with most of this being a degradant product at an approximate RRT of 3.07. This data indicates a surprising level of chemical incompatibility with magnesium stearate. Total impurities increased from 0.19% at T=zero to 2.88% at T=1 month in the presence of magnesium stearate, but on 0.17% at T=zero to 0.35% at T=1 month in the lactose blend without magnesium stearate.

Therefore, good chemical compatibility was observed in the absence of magnesium stearate, a common formulating agent, and with the simpler composition of only a lactose monohydrate carrier. By contrast to the typical functional effects of lactose and magnesium stearate excipients, magnesium stearate was ineffective to prevent agglomeration of epinephrine bitartrate and in fact created difficulties. Meanwhile lactose, a carrier excipient, was surprisingly effective in mitigating the tendency of epinephrine bitartrate to self-agglomerate and enabling a useful inhalable formulation with improved chemical and physical stability compared to those containing magnesium stearate.

TABLE 21

Results from related substances testing of 10% micronized epinephrine bitartrate + lactose monohydrate.

| Relative RT | Initial % Area Rep 1 | Initial % Area Rep 2 | Initial Mean | 1 week % Area Rep 1 | 1 week % Area Rep 2 | 1 week Mean | 2 week % Area Rep 1 | 2 week % Area Rep 2 | 2 week Mean | 1 month % Area Rep 1 | 1 month % Area Rep 2 | 1 month Mean |
|---|---|---|---|---|---|---|---|---|---|---|---|---|
| 0.86 | ND | ND | ND | 0.05 | 0.06 | 0.06 | ND | ND | ND | ND | ND | ND |
| 3.07 | ND | ND | ND | 0.06 | 0.07 | 0.07 | 0.09 | 0.09 | 0.09 | 0.21 | 0.22 | 0.22 |
| 3.11 (impurity A) | 0.17 | 0.17 | 0.17 | 0.17 | 0.20 | 0.19 | 0.20 | 0.18 | 0.19 | 0.13 | 0.13 | 0.13 |
| Sum | 0.17 | 0.17 | 0.17 | 0.28 | 0.33 | 0.31 | 0.29 | 0.27 | 0.28 | 0.34 | 0.35 | 0.35 |

ND - not detected

TABLE 22

Results from related substances testing of 10% micronized epinephrine bitartrate + lactose monohydrate + magnesium stearate.

| Relative RT | Initial % Area Rep 1 | Initial % Area Rep 2 | Initial Mean | 1 week % Area Rep 1 | 1 week % Area Rep 2 | 1 week Mean | 2 week % Area Rep 1 | 2 week % Area Rep 2 | 2 week Mean | 1 month % Area Rep 1 | 1 month % Area Rep 2 | 1 month Mean |
|---|---|---|---|---|---|---|---|---|---|---|---|---|
| 0.41 | ND | ND | ND | ND | ND | ND | ND | ND | ND | 0.14 | 0.14 | 0.14 |
| 0.65 | ND | ND | ND | ND | ND | ND | 0.06 | 0.06 | 0.06 | 0.08 | 0.08 | 0.08 |
| 0.86 | ND | ND | ND | 0.12 | 0.10 | 0.11 | ND | ND | ND | ND | ND | ND |
| 1.63 | ND | ND | ND | ND | ND | ND | 0.08 | 0.08 | 0.08 | 0.26 | 0.26 | 0.26 |
| 1.88/1.89 | ND | ND | ND | ND | ND | ND | ND | ND | ND | 0.09 | 0.09 | 0.09 |
| 3.06/3.08 | ND | ND | ND | 0.53 | 0.49 | 0.51 | 0.81 | 0.80 | 0.80 | 1.39 | 1.37 | 1.38 |
| 3.10 (impurity A) | 0.19 | 0.19 | 0.19 | 0.43 | 0.39 | 0.41 | 0.57 | 0.54 | 0.56 | 0.83 | 0.82 | 0.83 |
| 3.17/3.18 | ND | ND | ND | ND | ND | ND | ND | ND | ND | 0.10 | 0.10 | 0.10 |
| Sum | 0.19 | 0.19 | 0.19 | 1.08 | 0.98 | 1.03 | 1.52 | 1.48 | 1.50 | 2.89 | 2.86 | 2.88 |

ND - not detected

The tables of data clearly indicate a surprising level of chemical stability is achieved with epinephrine bitartrate blended with lactose alone, but not with the further addition of magnesium stearate to the epinephrine/lactose blend. This is surprising considering magnesium stearate is one of the most widely used excipients in pharmaceutical products and unusual to see this level of chemical incompatibility with magnesium stearate. Further it is surprising that a lubricant (or force control agent), most commonly as magnesium stearate in DPI products, was not required at all to mitigate the strong tendency of micronized crystalline epinephrine bitartrate to self-agglomerate. A simple blending with lactose monohydrate was found to be both chemically more stable than with magnesium stearate also added, and the self-agglomeration tendency of the API was no longer seen once blended simply with lactose monohydrate. It was unexpected and useful that a simpler composition of API with lactose has such a positive influence on chemical and physical stability.

The more complex processing method of spray drying, and which converts the crystalline solid state to essentially an amorphous solid state, is commonly used in DPI products and reported by others for epinephrine. Spray drying requires specialized expensive processing equipment and facilities. It is a processing technology that is less available at contract manufacture sites. It requires use of organic solvents in processing that may leave residuals in the powdered product, and also necessitates specific site licensing and abatement systems to permit processing with such solvents. Furthermore, the process yields of spray drying are generally less than conventional micronization, and the amorphous spray dried products are thermodynamically less stable than crystalline products. For all these reasons, micronization and lactose blending are preferred and simpler processing techniques than spray drying. The simple formulation and processing conceived here of micronization of crystalline epinephrine bitartrate and blending with lactose, filled into a capsule and loaded into a dry powder inhaler was found to deliver a process and product highly useful for pharmaceutical product purposes to deliver epinephrine via a DPI to a patient in need thereof.

Listing of Embodiments

1. An inhalable formulation, comprising:
   (i) epinephrine, and/or a pharmaceutically acceptable derivative and/or salt thereof; and
   (ii) a solid carrier.
2. The inhalable formulation of item 1, wherein the epinephrine, and/or a pharmaceutically acceptable derivative and/or salt thereof, is present at between about 0.01 to about 5.0 mg per unit dose of the formulation
3. The inhalable formulation of item 1 or item 2, wherein the epinephrine salt, or epinephrine derivative salt, is selected from the group consisting of bitartrate, hydrochloride, maleate, malate, malonate, borate and fumarate salts, and mixtures thereof.
4. The inhalable formulation of any one of the preceding items, wherein the epinephrine derivative is selected from the group consisting of norepinephrine, dopamine, 3-methoxytyramine, synephrine, p-octopamine and/or salts and mixtures thereof.
5. The inhalable formulation of any one of the preceding items, wherein the solid carrier is selected from the group consisting of alpha-lactose monohydrate, beta-lactose, an anhydrous lactose, mannitol, sucrose, and trehalose.
6. The inhalable formulation of any one of the preceding items, wherein the inhalable formulation consists essentially of epinephrine, and/or a pharmaceutically acceptable derivative and/or salt thereof; and a solid carrier.
7. The inhalable formulation of any one of the preceding items, wherein the inhalable formulation does not comprise any other excipients than the solid carrier.
8. The inhalable formulation of any one of the preceding items, wherein the inhalable formulation does not comprise a pH buffer agent.
9. The inhalable formulation of any one of the preceding items, wherein the inhalable formulation consists or consists essentially of epinephrine bitartrate and a solid carrier, preferably crystalline epinephrine bitartrate and a solid carrier.
10. The inhalable formulation of any one of the preceding items, wherein the inhalable formulation consists or consists essentially of epinephrine bitartrate and a lactose solid carrier, optionally alpha-lactose monohydrate solid carrier.
11. The inhalable formulation of any one of the preceding items, wherein the solid carrier is present within the inhalable formulation at between about 50% w/w to 99% w/w of the entire formulation.
12. A dry powder inhaler comprising the inhalable formulation of any one of the preceding items.
13. A process of forming the inhalable formulation of any one of item 1 to item 11, including the steps of:
   (a) micronizing the epinephrine, and/or pharmaceutically acceptable derivative and/or salt thereof, and
   (b) combining the micronized epinephrine, and/or pharmaceutically acceptable derivative and/or salt thereof, with the solid carrier.
14. An inhalable formulation of any one of item 1 to item 11, when produced by the process of item 13.
15. A method of delivering epinephrine, and/or a pharmaceutically acceptable derivative and/or salt thereof, to a subject in need thereof, including the step of:
   administering the inhalable formulation of any one of item 1 to item 11 to the subject,
   to thereby deliver the epinephrine, and/or a pharmaceutically acceptable derivative and/or salt thereof, to the subject.
16. A method of treating a disease, disorder or condition responsive to epinephrine, and/or a pharmaceutically acceptable derivative and/or salt thereof, in a subject in need thereof, including the step of:
   administering the inhalable formulation of any one of item 1 to item 11 to the subject;
   to thereby treat the disease, disorder or condition in the subject.
17. The method of item 16, wherein the disease, disorder or condition responsive to epinephrine, and/or a pharmaceutically acceptable derivative and/or salt thereof, is selected from the group consisting of anaphylaxis, cardiac arrest, glaucoma, asthma, bronchospasm, croup, and respiratory distress.
18. The method of item 16 or item 17, wherein the method of administering includes the steps of:
   providing the inhalable formulation of any one of item 1 to item 11 to the subject; and
   allowing the subject to inhale the inhalable formulation,
   to thereby treat the disease or condition in the subject.
19. The method of any one of item 16 to item 18, wherein the step of providing the inhalable formulation includes providing the dry powder inhaler of item 12 to the subject.
20. The method of any one of item 16 to item 19, wherein the method further includes the steps of: (i) monitoring the patient; and (ii) optionally administering further amounts of the inhalable formulation of any one of item 1 to item 11.

The invention claimed is:

1. A dry powder inhalable formulation consisting essentially of:
   (i) crystalline epinephrine bitartrate; and
   (ii) crystalline α-lactose monohydrate present at between about 50% w/w and about 99% w/w of the entire formulation.

2. The inhalable formulation of claim 1, wherein the crystalline α-lactose monohydrate is present at between about 75% w/w and about 99% w/w of the entire formulation.

3. A dry powder inhalable formulation consisting of:
   (i) crystalline epinephrine bitartrate; and
   (ii) crystalline α-lactose monohydrate present at between about 50% w/w and about 99% w/w of the entire formulation,
   wherein the dry powder inhalable formulation is substantially unchanged after storage for 6 months at 25° C. and 60% relative humidity.

4. The inhalable formulation of claim 1, wherein the crystalline epinephrine bitartrate is a micronized crystalline epinephrine bitartrate having a Dv50 of between about 1.5 μm and about 3 μm and a Dv90 of between about 2 μm and about 5 μm.

5. The inhalable formulation of claim 3, wherein the crystalline α-lactose monohydrate is present at between about 75% w/w and about 99% w/w of the entire formulation.

6. The inhalable formulation of claim 3, wherein the crystalline epinephrine bitartrate is a micronized crystalline epinephrine bitartrate having a Dv50 of between about 1.5 μm and about 3 μm and a Dv90 of between about 2 μm and about 5 μm.

7. The inhalable formulation of claim 1, wherein the inhalable formulation: (a) provides for a fine particle fraction, expressed as a percentage of the fine particle dose relative to the emitted dose, of greater than 30%; and (b) is stable for storage for 6 months at 25° C. and 60% relative humidity.

8. The inhalable formulation of claim 3, wherein the inhalable formulation provides for a fine particle fraction, expressed as a percentage of the fine particle dose relative to the emitted dose, of greater than 30%.

9. The inhalable formulation of claim 1, wherein:

(i) the crystalline α-lactose monohydrate is present at between about 75% w/w and about 99% w/w of the entire formulation;

(ii) the crystalline epinephrine bitartrate is a micronized crystalline epinephrine bitartrate having a Dv50 of between about 1.5 μm and about 3 μm and a Dv90 of between about 2 μm and about 5 μm; and (iii) the inhalable formulation: (a) provides for a fine particle fraction, expressed as a percentage of the fine particle dose relative to the emitted dose, of greater than 30%; and (b) is stable for storage for 6 months at 25° C. and 60% relative humidity.

10. The inhalable formulation of claim 3, wherein:

(i) the crystalline α-lactose monohydrate is present at between about 75% w/w and about 99% w/w of the entire formulation;

(ii) the crystalline epinephrine bitartrate is a micronized crystalline epinephrine bitartrate having a Dv50 of between about 1.5 μm and about 3 μm and a Dv90 of between about 2 μm and about 5 μm; and (iii) the inhalable formulation provides for a fine particle fraction, expressed as a percentage of the fine particle dose relative to the emitted dose, of greater than 30%.

11. A method of delivering epinephrine bitartrate to the lungs of a subject in need thereof, including the steps of:

providing the inhalable formulation of claim 1, within a dry powder negative pressure inhaler, to the subject; and allowing the subject to inhale at least a portion of the inhalable formulation from the dry powder negative pressure inhaler, to thereby deliver the epinephrine bitartrate to the lungs of the subject.

* * * * *